US009504825B2

(12) United States Patent
Ajiki et al.

(10) Patent No.: US 9,504,825 B2
(45) Date of Patent: Nov. 29, 2016

(54) PERCUTANEOUS PENETRATION ENHANCING APPARATUS AND PERCUTANEOUS PENETRATION ENHANCING METHOD

(71) Applicant: Panasonic Intellectual Property Management Co., Ltd., Osaka (JP)

(72) Inventors: Kaori Ajiki, Osaka (JP); Toshimitsu Minowa, Kanagawa (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 194 days.

(21) Appl. No.: 14/561,988

(22) Filed: Dec. 5, 2014

(65) Prior Publication Data

US 2015/0182737 A1    Jul. 2, 2015

(30) Foreign Application Priority Data

Dec. 27, 2013   (JP) ................. 2013-272318

(51) Int. Cl.
*A61N 1/00*    (2006.01)
*A61N 1/32*    (2006.01)
*A61N 1/30*    (2006.01)
(Continued)

(52) U.S. Cl.
CPC ............. *A61N 1/327* (2013.01); *A61K 8/0204* (2013.01); *A61M 35/00* (2013.01); *A61N 1/0412* (2013.01); *A61N 1/0476* (2013.01); *A61N 1/205* (2013.01); *A61N 1/303* (2013.01); *A61N 1/325* (2013.01); *A61N 1/328* (2013.01); *A61N 5/0616* (2013.01);
(Continued)

(58) Field of Classification Search
CPC .... A61N 5/0616; A61N 1/325; A61N 1/328; A61N 1/30; A61N 1/303; A61N 1/327; A61N 1/0448; A61N 1/0412; A61N 1/0428; A61N 2007/0034
See application file for complete search history.

(56) References Cited

U.S. PATENT DOCUMENTS 5,169,384 A     12/1992  Bosniak et al.
5,462,743 A  *  10/1995  Turner ................ A61F 13/0246
                                                        424/448
(Continued)

FOREIGN PATENT DOCUMENTS

DE     202008006017       8/2008
EP         2638929        9/2013
(Continued)

OTHER PUBLICATIONS

Satoshi Aihara et al., "Trend in Research on Organic Imaging Devices" NHK Science & Technology Research Laboratories R&D No. 132, pp. 4 to 11, Mar. 2012.
(Continued)

*Primary Examiner* — Kevin C Sirmons
*Assistant Examiner* — William Carpenter
(74) *Attorney, Agent, or Firm* — Greenblum & Bernstein, P.L.C.

(57) ABSTRACT

A percutaneous penetration enhancing apparatus includes a sheet member capable of being placed on a skin; a plurality of skin condition sensors arranged on the sheet member, each of the plurality of skin condition sensors detecting information related to a condition of the skin; and a plurality of percutaneous penetration enhancing elements arranged on the sheet member, each of the plurality of percutaneous penetration enhancing elements being operated on the basis of the information detected by one or more of the plurality of skin condition sensors.

8 Claims, 14 Drawing Sheets

(51) Int. Cl.
*A61N 1/04* (2006.01)
*A61N 1/20* (2006.01)
*A61K 8/02* (2006.01)
*A61M 35/00* (2006.01)
*A61N 5/06* (2006.01)
*A45D 44/00* (2006.01)

(52) U.S. Cl.
CPC ..... *A45D 2044/007* (2013.01); *A61K 2800/83* (2013.01)

(56) References Cited

U.S. PATENT DOCUMENTS

| | | | |
|---|---|---|---|
| 5,895,369 A * | 4/1999 | Flower | A61N 1/303 439/67 |
| 6,564,093 B1 * | 5/2003 | Ostrow | A61N 1/044 604/20 |
| 2007/0032846 A1 * | 2/2007 | Ferren | A61M 37/0076 607/89 |
| 2007/0225606 A1 * | 9/2007 | Naghavi | A61B 5/015 600/438 |
| 2007/0257256 A1 | 11/2007 | Kugler | |
| 2008/0152694 A1 * | 6/2008 | Lobl | A61F 9/0017 424/427 |
| 2009/0058274 A1 | 3/2009 | Yokoyama et al. | |
| 2009/0105605 A1 * | 4/2009 | Abreu | A61B 5/0008 600/549 |
| 2009/0224231 A1 | 9/2009 | Takeuchi et al. | |
| 2009/0281475 A1 | 11/2009 | Nisato et al. | |
| 2010/0305484 A1 | 12/2010 | Grollier et al. | |
| 2011/0077579 A1 * | 3/2011 | Harrison | A61M 5/14276 604/20 |
| 2013/0149268 A1 * | 6/2013 | Chen | A61K 8/97 424/62 |
| 2014/0276248 A1 * | 9/2014 | Hall | A61N 1/0432 601/2 |

FOREIGN PATENT DOCUMENTS

| | | |
|---|---|---|
| JP | 58-097650 | 6/1983 |
| JP | 11-019060 | 1/1999 |
| JP | 2005-516216 | 6/2005 |
| JP | 2005-334052 | 12/2005 |
| JP | 2007-178256 | 7/2007 |
| JP | 2007-300112 | 11/2007 |
| JP | 2009-048837 | 3/2009 |
| JP | 2011-505897 | 3/2011 |
| JP | 2011-194175 | 10/2011 |
| JP | 2013-506282 | 2/2013 |
| JP | 2013-168575 | 8/2013 |
| KR | 100963687 | 6/2010 |
| WO | 03/065041 | 8/2003 |
| WO | 2006/046521 | 5/2006 |
| WO | 2011/039182 | 4/2011 |
| WO | 2012/052986 | 4/2012 |
| WO | 2013/151128 | 10/2013 |

OTHER PUBLICATIONS

Takanori Kiyokura et al., "Wearable Laser Blood Flowmeter" NTT Technical Review, pp. 24-27, Nov. 2005.
Search report from E.P.O., mail date is May 12, 2015.

* cited by examiner

| BLOCK (551) | SKIN CONDITION SENSOR (552) | PERCUTANEOUS PENETRATION ENHANCING ELEMENT (553) |
|---|---|---|
| $1^{ST}$ BLOCK | $1^{ST}$ TO $3^{RD}$ SKIN CONDITION SENSORS | $1^{ST}$ AND $2^{ND}$ PERCUTANEOUS PENETRATION ENHANCING ELEMENTS |
| $2^{ND}$ BLOCK | $4^{TH}$ TO $6^{TH}$ SKIN CONDITION SENSORS | $3^{RD}$ AND $4^{TH}$ PERCUTANEOUS PENETRATION ENHANCING ELEMENTS |
| ⋮ | ⋮ | ⋮ |
| $L^{TH}$ BLOCK | ... TO $M^{TH}$ SKIN CONDITION SENSORS | ... AND $N^{TH}$ PERCUTANEOUS PENETRATION ENHANCING ELEMENTS |

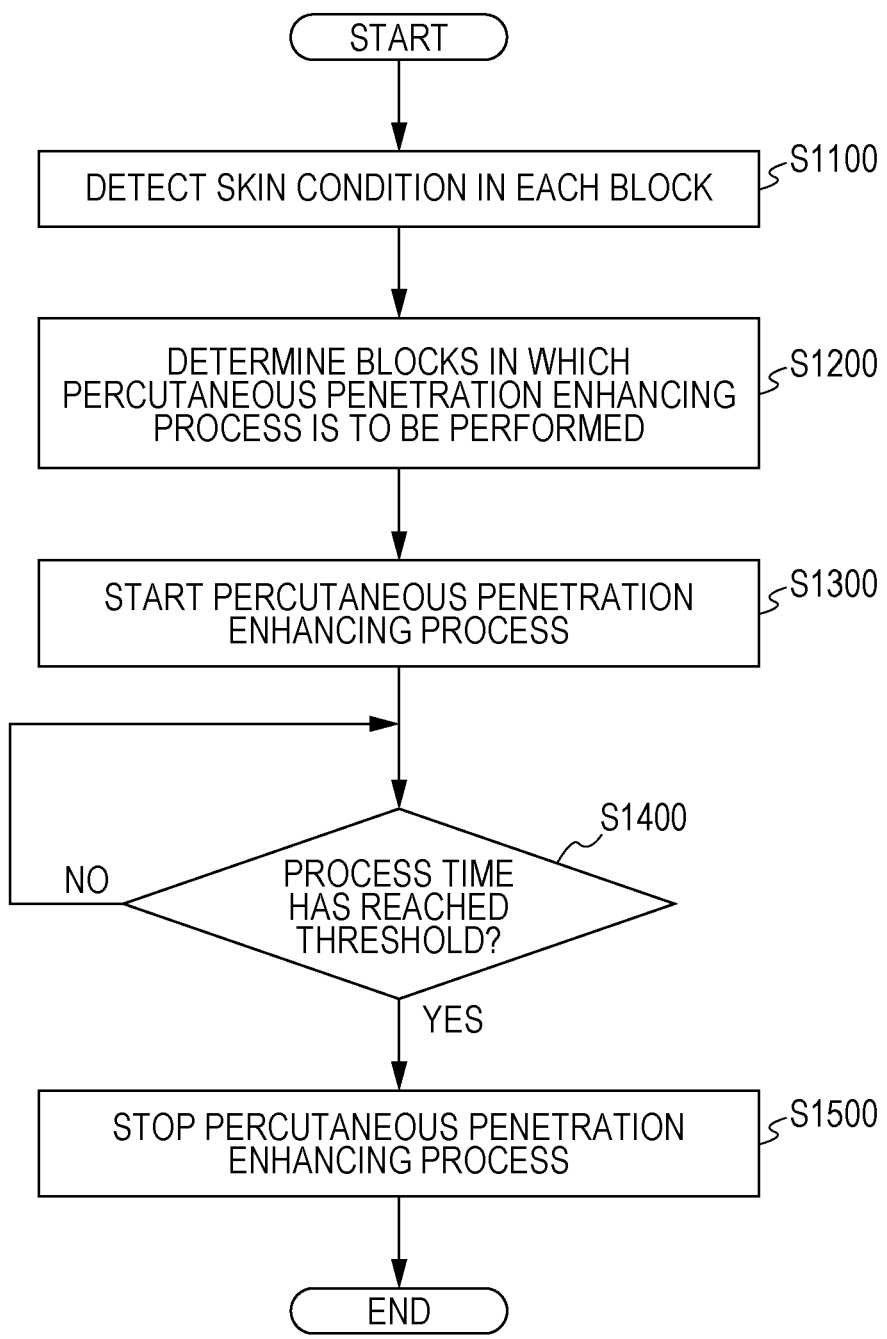

PERCUTANEOUS PENETRATION ENHANCING APPARATUS AND PERCUTANEOUS PENETRATION ENHANCING METHOD

BACKGROUND

1. Technical Field

The present disclosure relates to a percutaneous penetration enhancing apparatus and a percutaneous penetration enhancing method.

2. Description of the Related Art

In recent years, apparatuses for enhancing penetration of a cosmetic essence, agent, etc., applied to the skin into the skin (hereinafter referred to as a "percutaneous penetration enhancing apparatus") have come into wide use. Examples of percutaneous penetration enhancing apparatuses include those performing iontophoresis (see, for example, Japanese Unexamined Patent Application Publication No. 2005-334052 (hereinafter referred to as Patent Document 1)) and those performing electroporation (see, for example, Japanese Unexamined Patent Application Publication No. 2011-194175 (hereinafter referred to as Patent Document 2)).

SUMMARY

However, it is difficult to effectively perform a penetration enhancing process by using the technologies of the related art.

One non-limiting and exemplary embodiment provides a percutaneous penetration enhancing apparatus capable of effectively performing a penetration enhancing process.

Additional benefits and advantages of the disclosed embodiments will be apparent from the specification and figures. The benefits and/or advantages may be individually provided by the various embodiments and features of the specification and drawings disclosure, and need not all be provided in order to obtain one or more of the same.

In one general aspect, the techniques disclosed here feature a percutaneous penetration enhancing apparatus including a sheet member capable of being placed on a skin; a plurality of skin condition sensors arranged on the sheet member, each of the plurality of skin condition sensors detecting information related to a condition of the skin; and a plurality of percutaneous penetration enhancing elements arranged on the sheet member, each of the plurality of percutaneous penetration enhancing elements being operated on the basis of the information detected by one or more of the plurality of skin condition sensors.

Note that general and specific aspects of the present disclosure may be implemented in a form of a method.

With the percutaneous penetration enhancing apparatus according to the present disclosure, the penetration enhancing process can be effectively performed.

BRIEF DESCRIPTION OF THE DRAWINGS

FIG. 8 illustrates an example of the contents of an information table according to the second embodiment.

FIG. 9 is a flowchart of an example of an operation of the percutaneous penetration enhancing apparatus according to the second embodiment.

DETAILED DESCRIPTION

Background Knowledge

Figure 1:
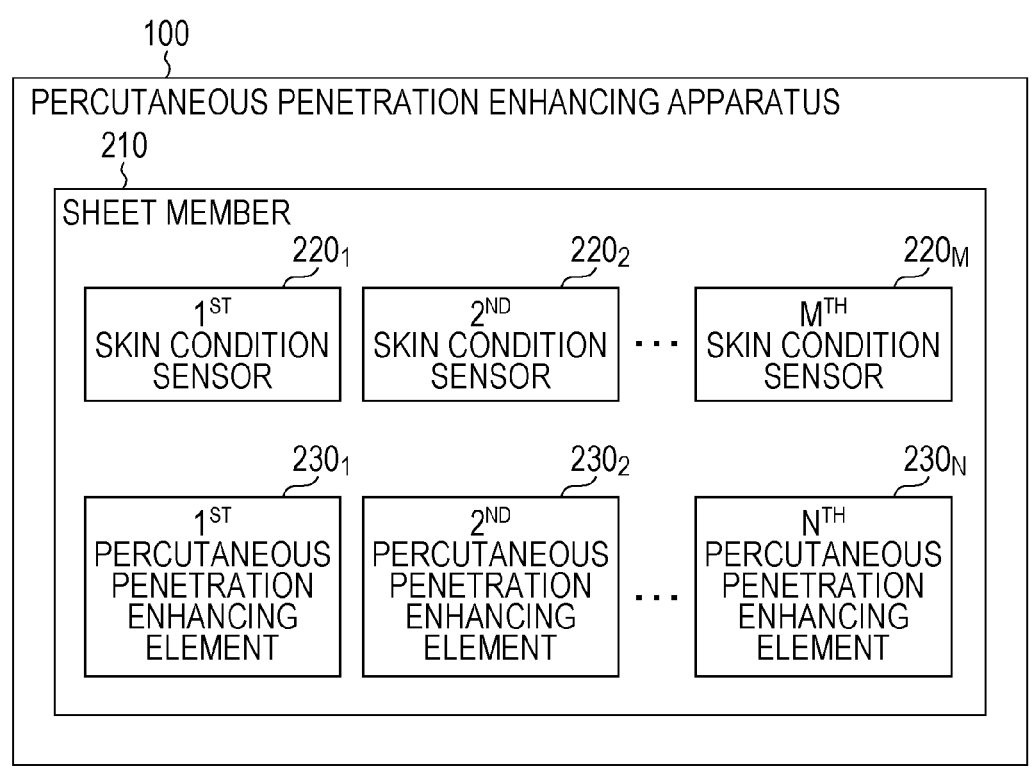
FIG. 1 illustrates an example of the structure of a percutaneous penetration enhancing apparatus according to a first embodiment of the present disclosure.

The percutaneous penetration enhancing apparatuses described in Patent Documents 1 and 2 (hereinafter referred to as the "related art"), include a cylindrical main body and a contact portion. The contact portion is arranged at an end of the main body, and is to be brought into contact with the skin. The percutaneous penetration enhancing apparatuses of the related art are configured to perform a process of applying an electric field to the skin through the contact portion and changing the condition of a part of the skin that is in contact with the contact portion so as to facilitate penetration of a cosmetic essence, agent, etc. (hereinafter referred to as a "cosmetic agent"). This process is hereinafter referred to as a "penetration enhancing process".

A user holds the main portion with his or her hand and brings the contact portion into contact with a part of the skin where the penetration enhancing process is to be performed. Thus, according to the related art, penetration of the cosmetic agent into the skin can be enhanced, and the skin condition can be improved.

In general, the skin has parts where the penetration enhancing process is to be performed and parts where the penetration enhancing process is not to be performed. For example, it is not preferable to perform the penetration enhancing process for a cosmetic agent having an effect of reducing blemishes on a part of the skin without blemishes.

However, according to the related art, there is a possibility that the penetration enhancing process will be performed on parts where the process is not necessary, or will not be performed on parts where the process is necessary. This is because it is difficult to appropriately determine the parts of the skin where the penetration enhancing process is to be performed. For example, blemishes in a deep part of the skin are difficult to see on the surface, and it is difficult for a user to find them. In addition, it takes time and effort to find the parts where the penetration enhancing process is to be performed and perform the penetration enhancing process on each part.

Thus, according to the related art, there is a possibility that the parts of the skin where the penetration enhancing process is performed do not match the parts where the penetration enhancing process is required. In other words, according to the related art, it is difficult to effectively perform the penetration enhancing process.

Accordingly, a percutaneous penetration enhancing apparatus according to the present disclosure includes a sheet member capable of being placed on a skin; a plurality of skin condition sensors arranged on the sheet member, each of the plurality of skin condition sensors detecting information related to a condition of the skin; and a plurality of percutaneous penetration enhancing elements arranged on the sheet member, each of the plurality of percutaneous penetration enhancing elements being operated on the basis of the information detected by one or more of the plurality of skin condition sensors.

Accordingly, the penetration enhancing process can be effectively performed.

Embodiments of the present disclosure will now be described in detail with reference to the accompanying drawings.

First Embodiment

A first embodiment of the present disclosure is an example of the basic embodiment of the present disclosure.

FIG. 1 illustrates an example of the structure of a percutaneous penetration enhancing apparatus according to the first embodiment.

Referring to FIG. 1, a percutaneous penetration enhancing apparatus 100 includes a sheet member 210, $1^{st}$ to $M^{th}$ skin condition sensors $220_1$ to $220_M$, and $1^{st}$ to $N^{th}$ percutaneous penetration enhancing elements $230_1$ to $230_N$.

The sheet member 210 is capable of being placed on a skin.

The $1^{st}$ to $M^{th}$ skin condition sensors $220_1$ to $220_M$ are arranged on the sheet member 210. Each of the $1^{st}$ to $M^{th}$ skin condition sensors $220_1$ to $220_M$ detects information related to a condition of the skin in a vicinity thereof.

The $1^{st}$ to $N^{th}$ percutaneous penetration enhancing elements $230_1$ to $230_N$ are also arranged on the sheet member 210. Each of the $1^{st}$ to $N^{th}$ percutaneous penetration enhancing elements $230_1$ to $230_N$ is located so as to correspond to one or more of the $1^{st}$ to $M^{th}$ skin condition sensors $220_1$ to $220_M$. Each of the $1^{st}$ to $N^{th}$ percutaneous penetration enhancing elements $230_1$ to $230_N$ operates in accordance with the information (a detection result or detection results) detected by one or more of the $1^{st}$ to $M^{th}$ skin condition sensors $220_1$ to $220_M$ corresponding thereto.

The percutaneous penetration enhancing apparatus 100 having the above-described structure is capable of performing the penetration enhancing process on each part of the skin in accordance with the condition of the part of the skin. Therefore, the penetration enhancing process can be effectively performed.

Second Embodiment

A second embodiment of the present disclosure is an example in which the present disclosure is applied to a percutaneous penetration enhancing apparatus which performs iontophoresis as the penetration enhancing process by using a face sheet that covers the entire surface of a face.

Appearance and Structure of Percutaneous Penetration Enhancing Apparatus

First, the appearance and structure of a percutaneous penetration enhancing apparatus according to the second embodiment will be described.

Appearance of Percutaneous Penetration Enhancing Apparatus

Figure 2:
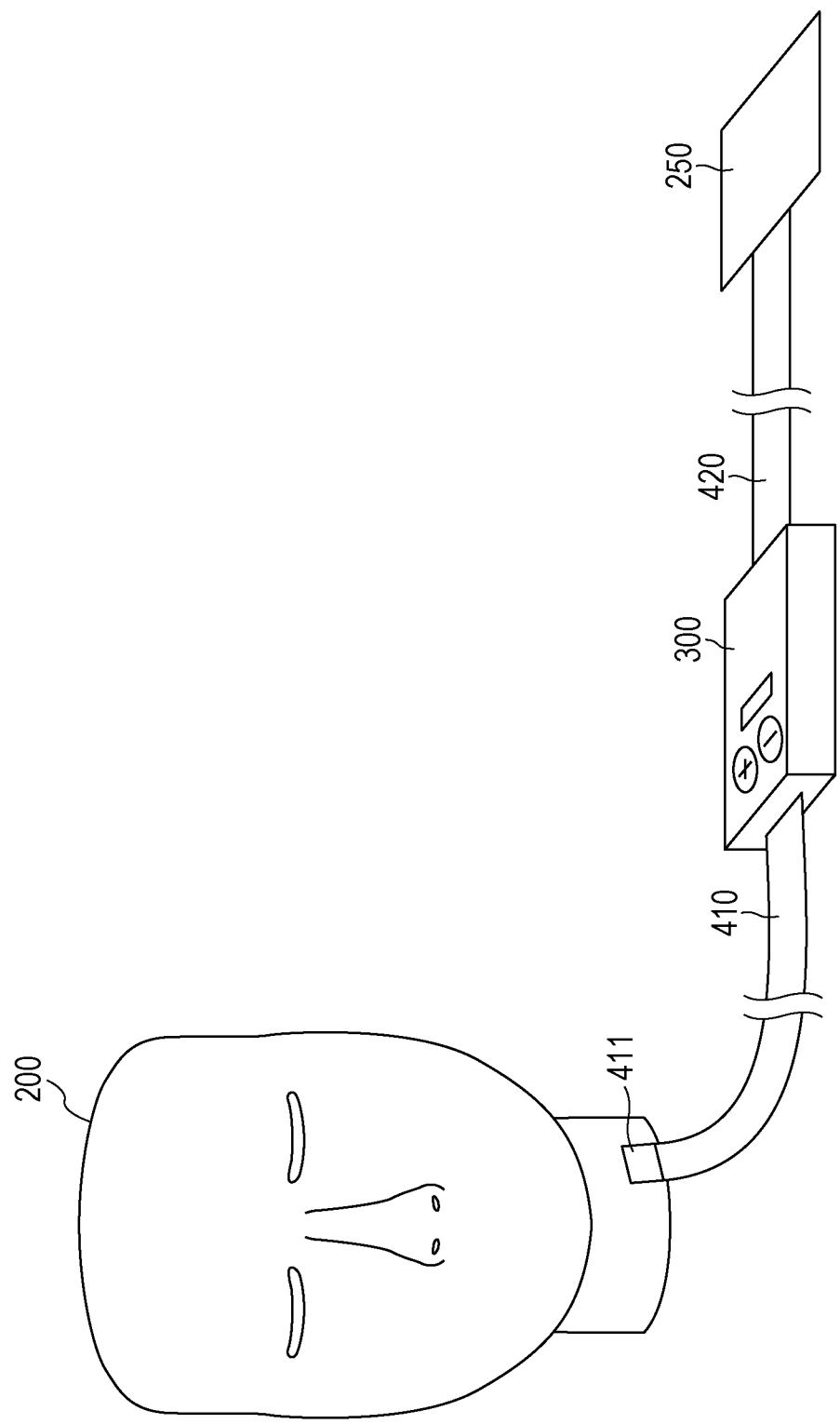
FIG. 2 illustrates an example of the appearance of a percutaneous penetration enhancing apparatus according to a second embodiment of the present disclosure.

FIG. 2 illustrates an example of the appearance of the percutaneous penetration enhancing apparatus according to the second embodiment.

As illustrated in FIG. 2, a percutaneous penetration enhancing apparatus 100 includes a sheet device 200, an electrode unit 250, and a control unit 300.

The sheet device 200 includes an elastic and flexible sheet member as a base material, the sheet member having a three-dimensional shape that covers the entire surface of a face. The sheet member that serves as the base material may be made of, for example, an energy ray-cured composition containing an acryloyl group-terminated urethane polymer and an acrylic monomer (see Japanese Unexamined Patent Application Publication No. 2013-168575). In the present embodiment, the sheet member is optically transparent.

The sheet device 200 has slits having the shape of closed eyes and openings corresponding to the nostrils. In other words, the sheet device 200 is shaped so as to cover the entire face including the upper eyelids, lower eyelids, lips, and neck.

The sheet device 200 is configured such that, when placed on the face in a certain position, the state in which the sheet device 200 is in close contact with the skin surface of the entire face can be maintained owing to the surface tension. To ensure sufficient adhesion, a biocompatible adhesive, such as a spirit gum, a silicone adhesive, or a latex adhesive, may be additionally used. The sheet device 200 is preferably selectable from a plurality of sheet devices having different sizes in accordance with the size of the face.

A plurality of skin condition sensors and a plurality of percutaneous penetration enhancing elements (not shown) are arranged on a surface of the sheet member of the sheet device 200 that comes into close contact with the face (hereinafter referred to as an "inner surface"). In the present embodiment, the percutaneous penetration enhancing elements are iontophoresis elements.

The electrode unit 250 has a size and shape such that the electrode unit 250 can be attached to, for example, the back of a hand, and includes a sheet member similar to that of the sheet device 200 as a base material. The electrode unit 250 is configured such that the state in which the electrode unit 250 is in close contact with the skin of a part other than the face, such as the back of a hand, can be maintained owing to surface tension. The above-mentioned adhesives may be additionally used to ensure close contact between the electrode unit 250 and the skin.

An enhancement assisting element (not shown), which corresponds to the percutaneous penetration enhancing elements on the sheet device 200, is arranged on an inner surface of the sheet member of the electrode unit 250. In the present embodiment, the enhancement assisting element is an iontophoresis element with a polarity opposite to the polarity of the iontophoresis elements arranged on the sheet device 200.

The principle of iontophoresis and the detailed structure of the sheet device 200, including the arrangement of the skin condition sensors and the percutaneous penetration enhancing elements, will be described in detail below.

The control unit 300 is a device protected by a housing made of a material such as plastic, and is connected to the sheet device 200 with a cable 410. More specifically, the control unit 300 is connected to each of the skin condition sensors and each of the percutaneous penetration enhancing elements on the sheet device 200. The control unit 300 is also connected to the electrode unit 250 with a cable 420. An operating unit, such as a key switch, is provided on the surface of the housing of the control unit 300.

The lengths of the cable 410 and the cable 420 are preferably such that in the state in which the sheet device 200 is placed on the face and the electrode unit 250 is placed on, for example, the back of a hand, the control unit 300 can be placed in a pocket of the user's clothes.

The sheet device 200 and the control unit 300 are preferably detachably attached to each other by a connector 411 and the cable 420. With this structure, the user can replace the sheet device 200 with a new one every time the user uses the sheet device 200.

Principle of Iontophoresis

Figure 3:
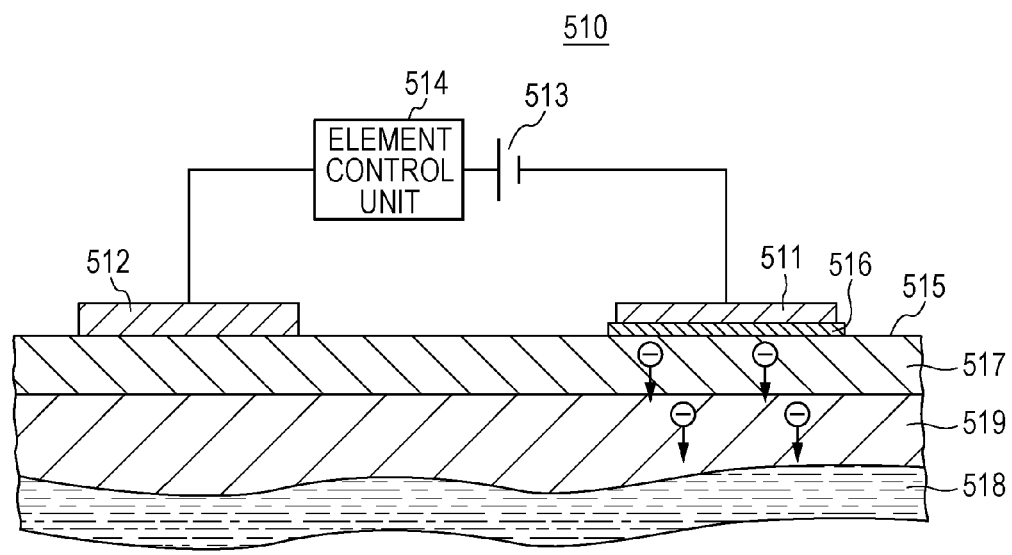
FIG. 3 illustrates the principle of iontophoresis according to the second embodiment.

FIG. 3 illustrates the principle of iontophoresis. Here, a case in which a percutaneous penetration enhancing process for anionic (negatively charged) cosmetic agent is performed will be described.

As illustrated in FIG. 3, an iontophoresis circuit 510 includes a first iontophoresis element 511, a second iontophoresis element 512, and a direct current power supply 513 and an element control unit 514 disposed between the first iontophoresis element 511 and the second iontophoresis element 512. The first iontophoresis element 511 and the second iontophoresis element 512 are in contact with the surface of a skin 515 of a single user. An anionic cosmetic agent 516 is provided between the first iontophoresis element 511 and the skin 515.

In this state, the element control unit 514 applies a voltage of several volts (V) between the first iontophoresis element 511, which serves as an anode, and the second iontophoresis element 512, which serves as a cathode, so that an electric field is applied to the skin. Accordingly, a current flows through the skin 515 in the region between the first iontophoresis element 511 and the second iontophoresis element 512, so that the cosmetic agent 516 penetrates the skin 515 in a vicinity of the first iontophoresis element 511 and endogenous ions are extracted from the skin 515 in a vicinity of the second iontophoresis element 512. As a result, the cosmetic agent 516 reaches not only an epidermal layer 517 but also a dermal layer 519, which is closer to capillaries 518 than the epidermal layer 517 is.

Thus, with iontophoresis, the cosmetic agent 516 can be delivered to a deep part of the skin 515 so that the cosmetic agent 516 reaches the dermal layer 519. Thus, with iontophoresis, the cosmetic agent reaches a deep part of the epidermal layer and the dermal layer, and blemishes and wrinkles can be effectively reduced.

In the present embodiment, the percutaneous penetration enhancing elements arranged on the sheet device 200 correspond to the first iontophoresis element 511, and the enhancement assisting element arranged on the electrode unit 250 corresponds to the second iontophoresis element 512 (see FIG. 2).

The skin 515 has characteristics similar to those of a capacitor. Therefore, when a voltage is continuously applied by the iontophoresis circuit 510, the skin 515 will be charged. This may make penetration of the cosmetic agent 516 difficult. To prevent this, according to the present embodiment, a pulse wave having a voltage of about 10 V, a current of about 0.3 to about 0.7 mA/cm$^2$, and a frequency of 1 kHz to 40 kHz (kilohertz) is applied so that the duty rate is 30% to 50%.

Structure of Sheet Device

Figure 4:
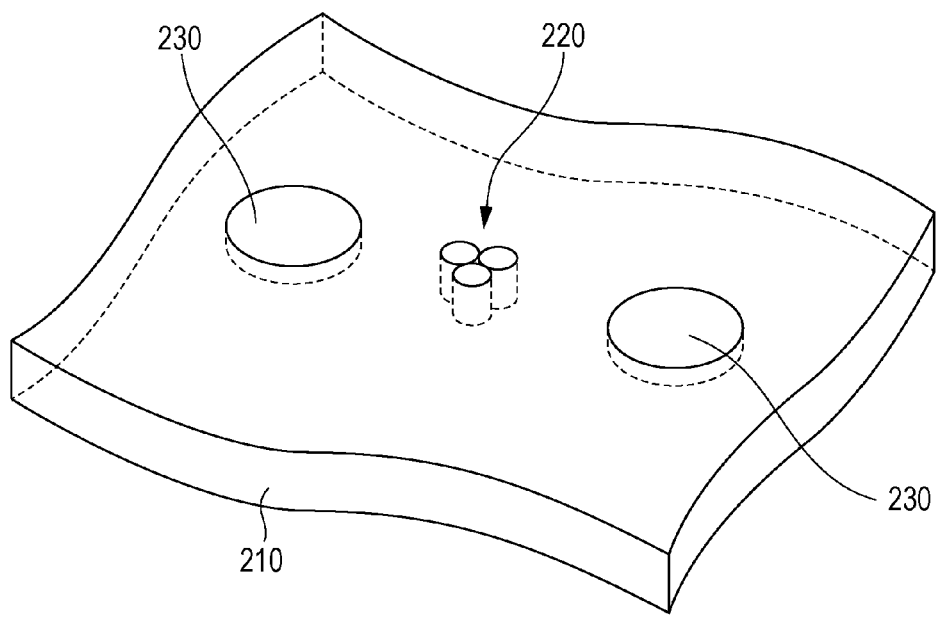
FIG. 4 illustrates an example of the structure of a sheet device according to the second embodiment.

FIG. 4 illustrates an example of the structure of the sheet device 200.

Referring to FIG. 4, the sheet device 200 is structured such that a skin condition sensor 220 including three light-receiving elements for different wavelengths and two percutaneous penetration enhancing elements 230 are embedded in the sheet member 210. Although a plurality of skin condition sensors and a plurality of percutaneous penetration enhancing elements are embedded in the entire sheet device 200, a portion of the sheet device 200 is illustrated in FIG. 4.

The skin condition sensor detects information related to a condition of the skin in a vicinity of the skin condition sensor. In the present embodiment, the skin condition sensor is a color tone sensor that detects a color tone of the skin as the information of the condition in the vicinity of the skin condition sensor. Since the sheet member 210 is optically transparent, ambient light, such as light from interior lights and external light, reaches the surface of the skin. The skin condition sensor receives the reflected light of the ambient light that has been reflected by the skin, and detects the color tone of the skin by spectroscopic analysis.

In order for the color tone sensor to be capable of receiving the reflected light from the skin, the color tone sensor is preferably arranged in the sheet device 200 so as not to be in close contact with the skin. For example, in the state in which the sheet member 210 is in close contact with the skin, the skin condition sensor is arranged such that a light receiving surface thereof faces the skin with an interval of about 100 micrometers therebetween.

Each percutaneous penetration enhancing element performs the penetration enhancing process on the skin in a vicinity of the percutaneous penetration enhancing element. In the present embodiment, as described above, the percutaneous penetration enhancing elements are iontophoresis elements. Electrode surfaces of the percutaneous penetration enhancing elements are exposed at the inner surface (upper surface in FIG. 4) of the sheet member 210.

The skin condition sensor and the percutaneous penetration enhancing elements are preferably as small as possible.

Examples of a small skin condition sensor (tone sensor) include a device that measures the intensities of light components having the wavelengths of R, G, and B with optical sensors, and a device described in "Trend in Research on Organic Imaging Devices" written by Satoshi Aihara and Misao Kubota in NHK STRL R&D No. 132, NHK Science & Technology Research Laboratories, March 2012, pp. 4-11 (hereinafter referred to as Non-Patent Document 1). In this device, three primary colors, R, G, and B, are captured with organic semiconductors. The color tone sensor according to Non-Patent Document 1 can be produced with high precision by printing.

The cosmetic agent may be applied to either the surface of the skin or the inner surface of the sheet device 200. However, it is difficult to supply a sufficient amount of cosmetic agent to the skin simply by applying the cosmetic agent.

Accordingly, the sheet device 200 is configured such that a large amount of cosmetic agent can be supplied to the skin.

Figure 5:
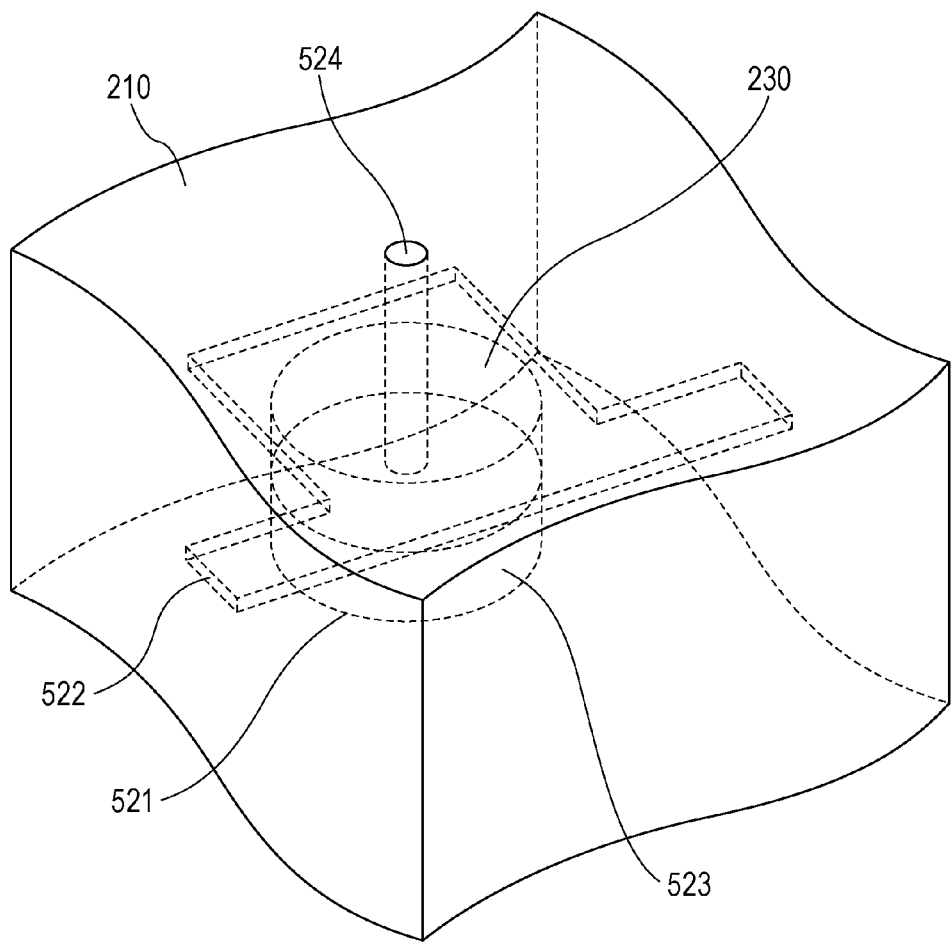
FIG. 5 illustrates an example of the structure of a percutaneous penetration enhancing element and a region around the percutaneous penetration enhancing element according to the second embodiment.

FIG. 5 illustrates an example of the structure of a percutaneous penetration enhancing element 230 and a region around the percutaneous penetration enhancing element 230.

As illustrated in FIG. 5, the percutaneous penetration enhancing element 230 is disc-shaped, and is connected to a wire 522 provided in the sheet member 210. The percutaneous penetration enhancing element 230 is fitted in a hole 521, which is formed in the inner surface (lower surface in FIG. 5) of the sheet member 210, so as to be recessed from the inner surface. In other words, a space 523 is provided between the percutaneous penetration enhancing element 230 and the skin.

This space 523 communicates with a space outside a surface of the sheet member 210 that does not contact the skin (upper surface in FIG. 5, hereinafter referred to as "outer surface"). More specifically, a hole 524, which has the same shape as that of a hole formed at the center of the percutaneous penetration enhancing element 230, is formed in the sheet member 210. The outer surface is a surface that is externally exposed in the state in which the sheet device 200 is placed on the face.

The hole 524 serves as an agent introduction port for introducing the cosmetic agent into the space 523 from the outside. Since the hole at the center of the percutaneous penetration enhancing element 230, the space 523, and the hole 524 are very small, the cosmetic agent that has been introduced through the hole 524 is quickly delivered to the space 523. Therefore, when, for example, the user applies the cosmetic agent to the outer surface of the sheet device 200 with a finger, the cosmetic agent can be easily supplied to the space between the percutaneous penetration enhancing element 230 and the skin.

A cosmetic agent retainer which absorbs and retains the cosmetic agent may be disposed in the hole 524 and the space 523.

Figure 6:
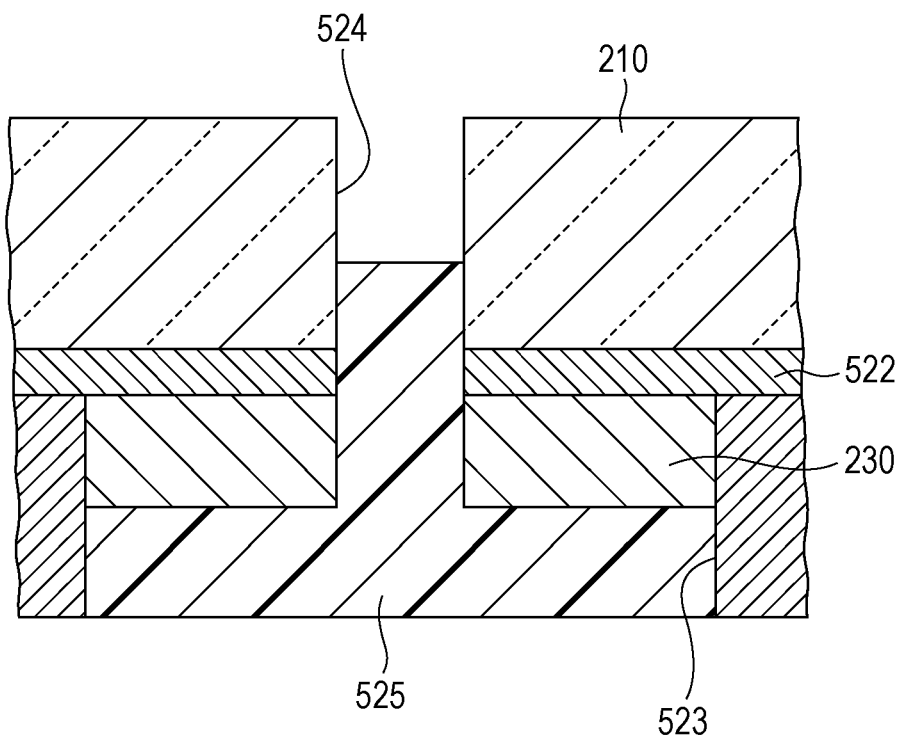
FIG. 6 illustrates a first modification of the structure of the percutaneous penetration enhancing element and the region around the percutaneous penetration enhancing element according to the second embodiment.

FIG. 6 illustrates an example of the structure of the percutaneous penetration enhancing element 230 and a region around the percutaneous penetration enhancing element 230 in the case where the cosmetic agent retainer is provided.

As illustrated in FIG. 6, a cosmetic agent retainer 525 is arranged so as to fill, for example, a deep part of the hole 524 and the space 523. The cosmetic agent retainer 525 is made of, for example, a material with a high moisture absorbency, such as polyurethane fiber. The cosmetic agent introduced through the hole 524 is absorbed and retained by the cosmetic agent retainer 525. The cosmetic agent retained by the cosmetic agent retainer 525 is delivered to the deep part of the skin by the electric charges output from the percutaneous penetration enhancing element 230.

Units of Control of Sheet Device

In the present embodiment, the sheet device 200 is controlled in units of small segments into which the sheet device 200 is divided. The segments and units of control of the sheet device 200 are hereinafter referred to as "blocks". Each block may be a square with sides of several millimeters to 1 cm.

Each block has at least one skin condition sensor and at least one percutaneous penetration enhancing element arranged therein. The arrangement density of the skin condition sensors and the percutaneous penetration enhancing elements in the sheet device 200 may be uniform. Alternatively, the arrangement density may differ between the blocks, or be non-uniform in each block. In the present embodiment, it is assumed that the sheet device 200 includes L blocks.

Functional Structure of Percutaneous Penetration Enhancing Apparatus

Figure 7:
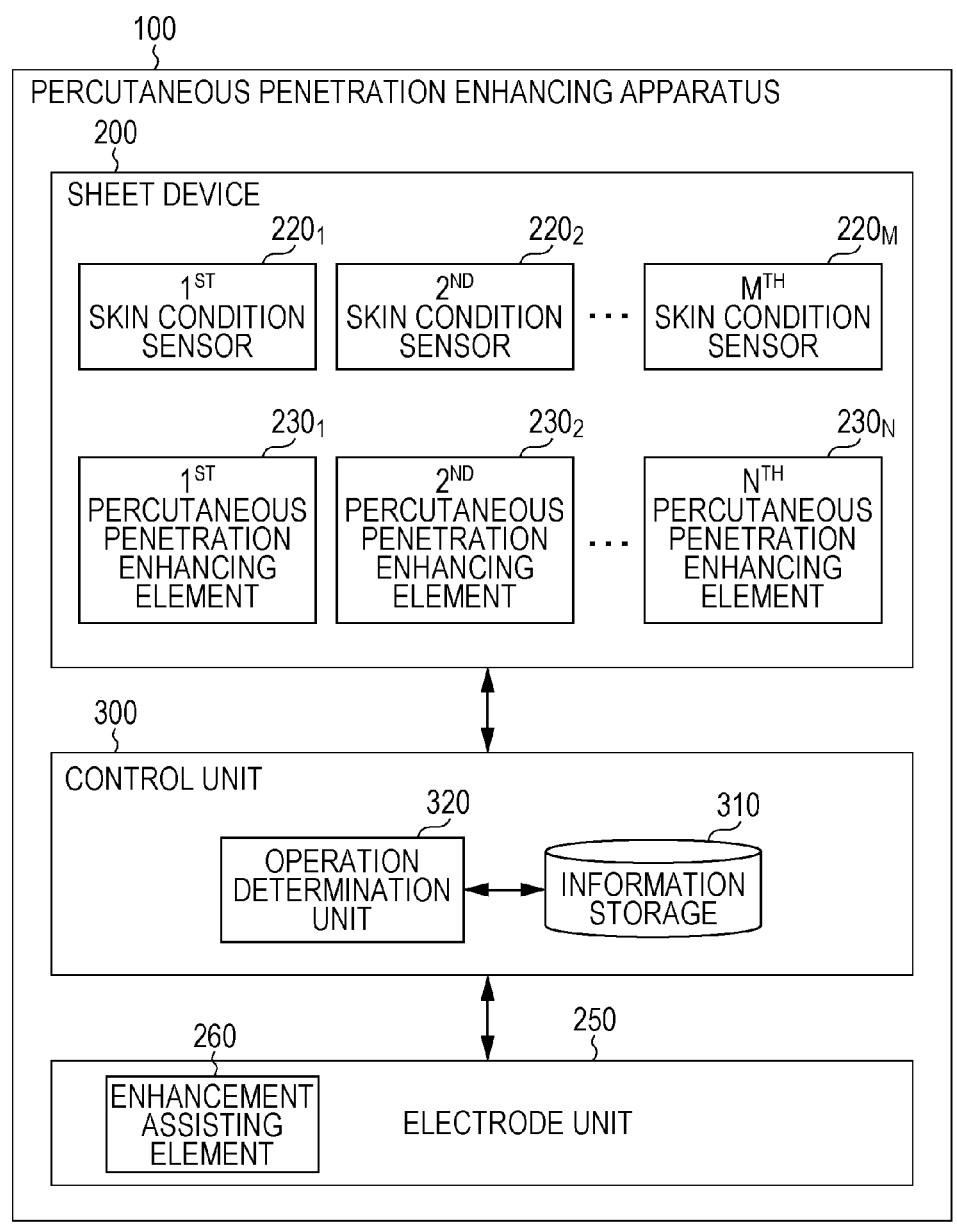
FIG. 7 illustrates an example of the functional structure of the percutaneous penetration enhancing apparatus.

FIG. 7 illustrates an example of the functional structure of the percutaneous penetration enhancing apparatus 100.

Referring to FIG. 7, the percutaneous penetration enhancing apparatus 100 includes the $1^{st}$ to $M^{th}$ skin condition sensors $220_1$ to $220_M$ and the $1^{st}$ to $N^{th}$ percutaneous penetration enhancing elements $230_1$ to $230_N$ arranged on the sheet device 200, and an enhancement assisting element 260 arranged on the electrode unit 250. The percutaneous penetration enhancing apparatus 100 also includes an information storage 310 and an operation determination unit 320, which are in the control unit 300.

The information storage 310 stores a table showing which of the skin condition sensors and which of the percutaneous penetration enhancing elements belong to each of the above-described blocks (hereinafter referred to as a "block information table") in advance.

FIG. 8 illustrates an example of the contents of the information table.

As illustrated in FIG. 8, a block information table 550 contains skin-condition-sensor identification information 552 and percutaneous-penetration-enhancing-element identification information 553 in association with block identification information 551. Each block has at least one skin condition sensor and at least one percutaneous penetration enhancing element arranged therein.

The operation determination unit 320 illustrated in FIG. 7 is connected to each of the $1^{st}$ to $M^{th}$ skin condition sensors $220_1$ to $220_M$ and each of the $1^{st}$ to $N^{th}$ percutaneous penetration enhancing elements $230_1$ to $230_N$ by the cable 410 (see FIG. 2) that connects the control unit 300 and the sheet device 200 to each other and cables (not shown) embedded in the sheet device 200.

Accordingly, the operation determination unit 320 is capable of outputting a control signal to each skin condition sensor to control the operation of the skin condition sensor, and receiving a detection value output from each skin condition sensor. The operation determination unit 320 is also capable of outputting a control signal to each percutaneous penetration enhancing element to control the operation of the percutaneous penetration enhancing element.

The operation determination unit 320 is also connected to the enhancement assisting element 260 by the cable 420 (see FIG. 2) that connects the control unit 300 and the electrode unit 250 to each other. Accordingly, the operation determination unit 320 is also capable of outputting a control signal to the enhancement assisting element 260 to control the operation of the enhancement assisting element 260.

The percutaneous penetration enhancing elements and the enhancement assisting element respectively correspond to the first iontophoresis element 511 and the second iontophoresis element 512 illustrated in FIG. 3. The operation determination unit 320 provides the functions of the element control unit 514 and the direct current power supply 513 illustrated in FIG. 3.

The operation determination unit 320 is capable of controlling each percutaneous penetration enhancing element by operating an element control unit corresponding to the percutaneous penetration enhancing element. For example, when a certain percutaneous penetration enhancing element corresponds to the first iontophoresis element 511, the element control unit 514 corresponds to this percutaneous penetration enhancing element. Thus, whether or not to perform the penetration enhancing process by iontophoresis (hereinafter referred to simply as "penetration enhancing process") can be controlled for each of the above-described blocks.

The operation determination unit 320 refers to the block information table 550 (see FIG. 8) and determines the operation of one or more percutaneous penetration enhancing elements arranged in each block of the sheet device 200 on the basis of detection values obtained by one or more skin condition sensors arranged in the block. More specifically, the operation determination unit 320 determines that a region in which the skin color is relatively dark is a region in which a blemish is present, and determines to perform the penetration enhancing process in the corresponding block.

Although not illustrated, the control unit 300 includes a central processing unit (CPU), a read only memory (ROM) that stores a control program, and a working memory, such as a random access memory (RAM). In this case, the function of each part of the control unit 300 is realized by causing the CPU to execute the control program.

In addition, although not illustrated, the control unit 300 includes a power supply unit, such as a battery. The power supply unit supplies electric power for operating the CPU, the sheet device 200, and the electrode unit 250.

With the above-described structure, the percutaneous penetration enhancing apparatus 100 is capable of performing the penetration enhancing process on the skin only in regions where blemishes are present.

The percutaneous penetration enhancing apparatus 100 preferably includes a switch circuit for switching the polarities of the $1^{st}$ to $N^{th}$ percutaneous penetration enhancing elements $230_1$ to $230_N$ and the enhancement assisting element 260. In addition, the operating unit of the control unit 300 preferably receives from the user information regarding whether the cosmetic agent is anionic (negatively charged) or cationic (positively charged), that is, whether the polarity of the percutaneous penetration enhancing elements is to be negative or positive.

For example, the operating unit of the control unit 300 includes a button marked "+" which allows the user to select the negative polarity and a button marked "−" which allows the user to select the positive polarity. In this case, when the button marked "−" is pressed, the operation determination unit 320 sets the $1^{st}$ to $N^{th}$ percutaneous penetration enhancing elements $230_1$ to $230_N$ to the negative polarity and the enhancement assisting element 260 to the positive polarity. When the button marked "+" is pressed, the operation determination unit 320 sets the $1^{st}$ to $N^{th}$ percutaneous penetration enhancing elements $230_1$ to $230_N$ to the positive polarity and the enhancement assisting element 260 to the negative polarity.

Thus, the percutaneous penetration enhancing apparatus 100 is capable of performing the penetration enhancing process for both an anionic cosmetic agent and a cationic cosmetic agent.

Operation of Percutaneous Penetration Enhancing Apparatus

Next, the operation of the percutaneous penetration enhancing apparatus 100 will be described.

First, the user places the sheet device 200 and the electrode unit 250 on the skin, and applies a cosmetic agent to the outer surface of the sheet device 200. The applied cosmetic agent flows into the small holes 524 (see FIGS. 5 and 6) formed in the sheet device 200 and reaches the spaces between the skin and the percutaneous penetration enhancing elements 230.

In this state, the user operates the control unit 300 to set the polarity of the percutaneous penetration enhancing elements 230 and give an instruction to start the operation. Accordingly, the percutaneous penetration enhancing apparatus 100 executes the process described below.

FIG. 9 is a flowchart of an example of the operation of the percutaneous penetration enhancing apparatus 100.

First, in Step S1100, each of the $1^{st}$ to $M^{th}$ skin condition sensors $220_1$ to $220_M$ detects the color tone of the skin and outputs the detection result to the operation determination unit 320.

Then, in Step S1200, the operation determination unit 320 selects, from the above-described blocks of the sheet device 200, one or more blocks in which the penetration enhancing process is to be performed.

For example, the operation determination unit 320 calculates the average of the detection results obtained by the $1^{st}$ to $M^{th}$ skin condition sensors $220_1$ to $220_M$, and multiplies the calculated average by a predetermined coefficient to determine a color density to be used as a criterion for the determination of blemishes. Then, the operation determination unit 320 determines that blocks in which the density of the detected color is greater than the determined density are blocks in which the penetration enhancing process is to be performed. With this process, regions in which the skin color is darker than that in other regions are detected as regions having blemishes, and those regions can be determined as the regions to be subjected to the penetration enhancing process.

In the case where a single block has a plurality of skin condition sensors, the operation determination unit 320 may determine whether or not to perform the penetration enhancing process in that block on the basis of the average of the detection values obtained by the skin condition sensors arranged in that block.

The average of the detection results used to determine the color density that serves as the criterion for the determination of blemishes may be calculated on the basis of the detection results of specific skin condition sensors selected from the $1^{st}$ to $M^{th}$ skin condition sensors $220_1$ to $220_M$.

The coefficient used to determine the color density that serves as the criterion for the determination of blemishes is determined in advance through, for example, experiments. The operation determination unit 320 may receive a parameter corresponding to the coefficient from the user through the operating unit.

Then, in Step S1300, the sheet device 200 starts the penetration enhancing process in the blocks selected as the blocks in which the penetration enhancing process is to be performed. More specifically, one or more percutaneous penetration enhancing elements arranged in each of the selected blocks and the enhancement assisting element 260 start to operate as an iontophoresis circuit. A single enhancement assisting element may be shared by all of the percutaneous penetration enhancing elements. Alternatively, a plurality of enhancement assisting elements may be provided so that each enhancement assisting element corresponds to one or more of the percutaneous penetration enhancing elements.

In the blocks in which the penetration enhancing process has been started, penetration of the cosmetic agent into the skin is enhanced. In the blocks in which the penetration enhancing process has not been started, penetration of the cosmetic agent into the skin is not enhanced.

Then, in Step S1400, the operation determination unit 320 determines whether or not the time elapsed since the start of the penetration enhancing process has reached a predetermined threshold (for example, 7 minutes).

The threshold corresponds to the time which is sufficient but not excessive for a single penetration enhancing process, and is determined in advance through, for example, experiments. A single threshold may be set for all of the blocks, or different thresholds may be set for the respective blocks.

When the process time has not yet reached the threshold (No in Step S1400), the operation determination unit 320 repeats the determination process in Step S1400. When the process time has reached the predetermined threshold (Yes in Step S1400), the operation determination unit 320 proceeds to Step S1500.

In Step S1500, the sheet device 200 stops the penetration enhancing process for all of the blocks, and ends the procedure.

With the above-described operation, the percutaneous penetration enhancing apparatus 100 is capable of performing the cosmetic agent penetration enhancing process on the skin only in regions where blemishes are present and stopping the penetration enhancing process before the process is excessively performed.

Preferably, the percutaneous penetration enhancing apparatus 100 moves a region in which the percutaneous penetration enhancing elements are operated to supply electricity (hereinafter referred to as "electrified region") in each block.

In this case, in the sheet device 200, it is necessary to divide each block into a plurality of small sub-blocks, each including one or more percutaneous penetration enhancing elements. While the determination process performed in Step 1400 in FIG. 9 is being repeated, the operation determination unit 320 switches the sub-block that serves as the electrified region once every certain time interval (for example, every 1 to 2 minutes) in each of the blocks in which the penetration enhancing process is to be performed.

Figure 10:
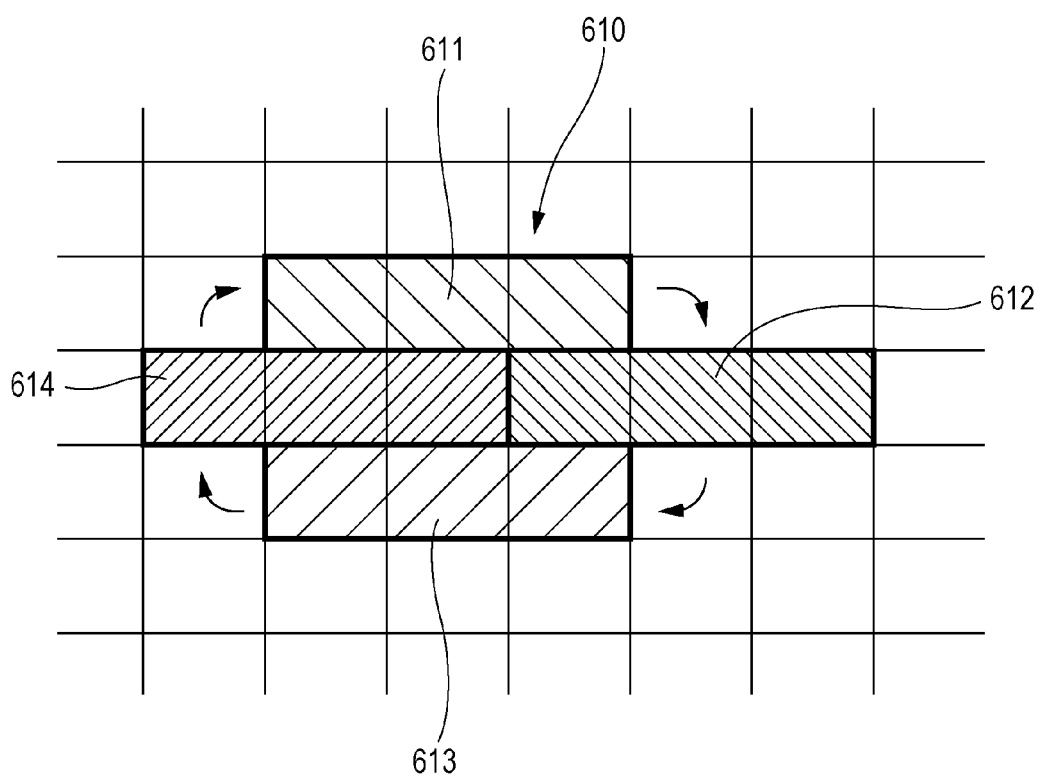
FIG. 10 illustrates an example of the manner in which sub-block switching is performed in the second embodiment.

FIG. 10 illustrates an example of the manner in which the sub-block that serves as the electrified region is switched.

In the example illustrated in FIG. 10, a block 610 includes first to fourth sub-blocks 611 to 614. Each of the first to fourth sub-blocks 611 to 614 includes at least one percutaneous penetration enhancing element.

Here, it is assumed that the operation determination unit 320 has determined that the penetration enhancing process is to be performed in the block 610. In this case, for example, as shown by the arrows in FIG. 10, the operation determination unit 320 successively sets the first to fourth sub-blocks 611 to 614 as the sub-block in which the percutaneous penetration enhancing element or elements is/are to be activated. For example, while the penetration enhancing process is being performed by the percutaneous penetration enhancing element or elements in the first sub-block 611, the percutaneous penetration enhancing elements in the second to fourth sub-blocks 612 and 614 do not perform the penetration enhancing process.

In this case, the time threshold used in Step S1400 in FIG. 9 needs to be set to a value determined in consideration of the time in which the penetration enhancing process is not performed. In the example illustrated in FIG. 10, for example, the time threshold used in Step S1400 in FIG. 9 is set to 28 minutes, which is calculated by multiplying 7 minutes by 4.

Accordingly, the total process time of a single penetration enhancing process can be increased while reducing the stress on the skin by reducing the time in which each part of the skin is continuously electrified.

The user carries out the penetration enhancing process once every day, for example, by using the percutaneous penetration enhancing apparatus 100 for 2 weeks to 1 month. As a result, blemishes on the face, for example, can be reduced.

Advantages of Percutaneous Penetration Enhancing Apparatus

As described above, with the percutaneous penetration enhancing apparatus according to the present embodiment, the penetration enhancing process can be appropriately performed on parts of the skin where the penetration enhancing process is required, without causing the user to determine the parts of the skin where the penetration enhancing process is to be performed. In other words, the percutaneous penetration enhancing apparatus according to the present embodiment is capable of effectively performing the penetration enhancing process.

With some cosmetic agents, the amount of supply to the parts of the skin where the penetration enhancing process is not required is to be made as small as possible. With the percutaneous penetration enhancing apparatus according to the present embodiment, the amount of cosmetic agent supplied to the parts of the skin where the penetration enhancing process is not required can be reduced to a very small amount. Therefore, the percutaneous penetration enhancing apparatus according to the present embodiment is particularly suitable for cosmetic agents of the above-mentioned type. In addition, the percutaneous penetration enhancing apparatus also provides effects of reducing excess application of cosmetic agent and unnecessary operation of the percutaneous penetration enhancing elements.

In addition, the user can carry out the penetration enhancing process without the use of hands by using the percutaneous penetration enhancing apparatus according to the present embodiment, and can therefore perform other activities or operations during the penetration enhancing process. In addition, with the percutaneous penetration enhancing apparatus according to the present embodiment, the penetration enhancing process can be prevented from being performed intensively on the side of the face that corresponds to the user's dominant hand or insufficiently in regions having irregular shapes, such as regions around nostrils.

Additional Use of Skin Temperature Detection

When the penetration enhancing process, such as iontophoresis, is performed, the skin temperature may increase due to promotion of the skin's metabolism. There is also a possibility that the user will strongly rub a part of the sheet device 200 to further enhance the penetration of the cosmetic agent and the sheet device 200 will malfunction as a result. In such a case, the temperature may suddenly increase.

Accordingly, the percutaneous penetration enhancing apparatus 100 may detect the skin temperature and stop the operation of the sheet device 200 by, for example, stopping the supply of electric power to the sheet device 200 irrespective of the process time when the skin temperature exceeds a predetermined threshold, such as 42 degrees.

In this case, the sheet device 200 includes a temperature sensor, which detects the skin temperature and outputs the detection result to the operation determination unit 320, for each block or for every few blocks that are adjacent to each other. The temperature sensor may be, for example, one in which an organic molecular layer of an organic thin-film transistor is formed of a phthalocyanine nano-size structure (see, for example, International Publication No. 2013/151128).

The operation determination unit 320 may stop the operation of the sheet device 200 only in the blocks in which the skin temperature has become greater than or equal to the predetermined threshold. Alternatively, the operation of the sheet device 200 may be stopped also in the surrounding blocks, or in all of the blocks.

Another Exemplary Structure of Sheet Device and Electrode

The electrode unit 250 (see FIG. 2) may be formed integrally with the sheet device 200.

Figure 11:
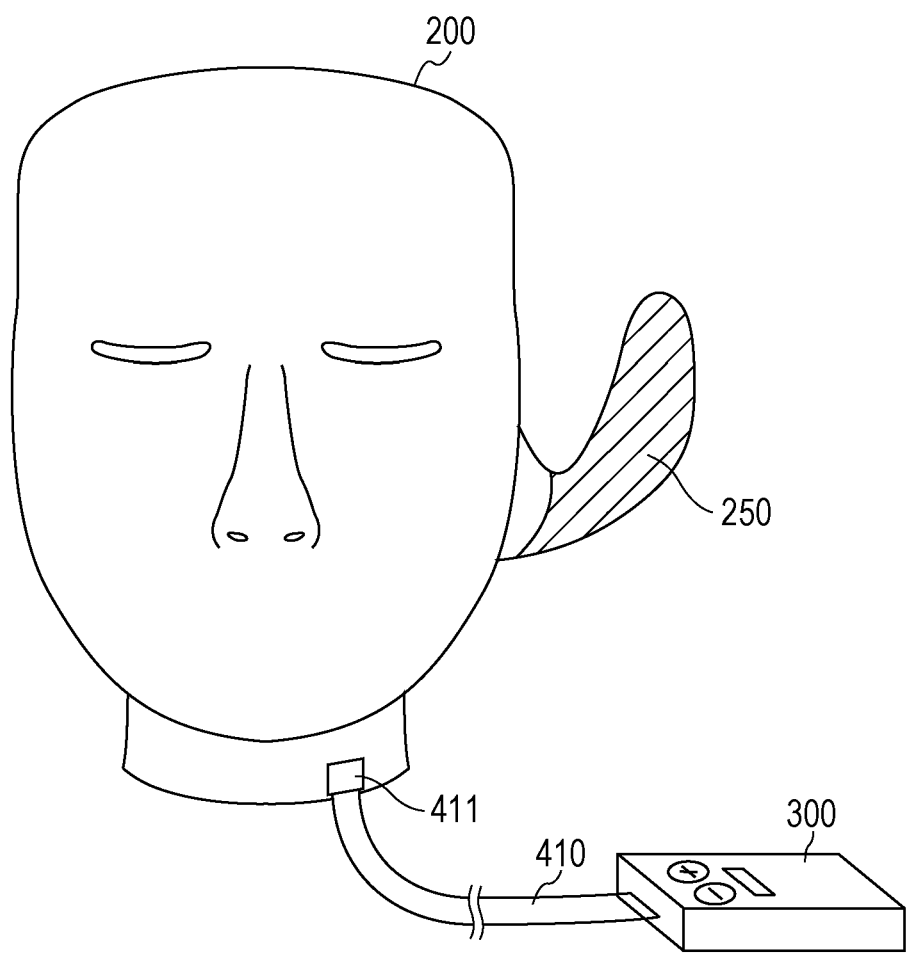
FIG. 11 illustrates a first modification of the appearance of the percutaneous penetration enhancing apparatus according to the second embodiment of the present disclosure.
Figure 12:
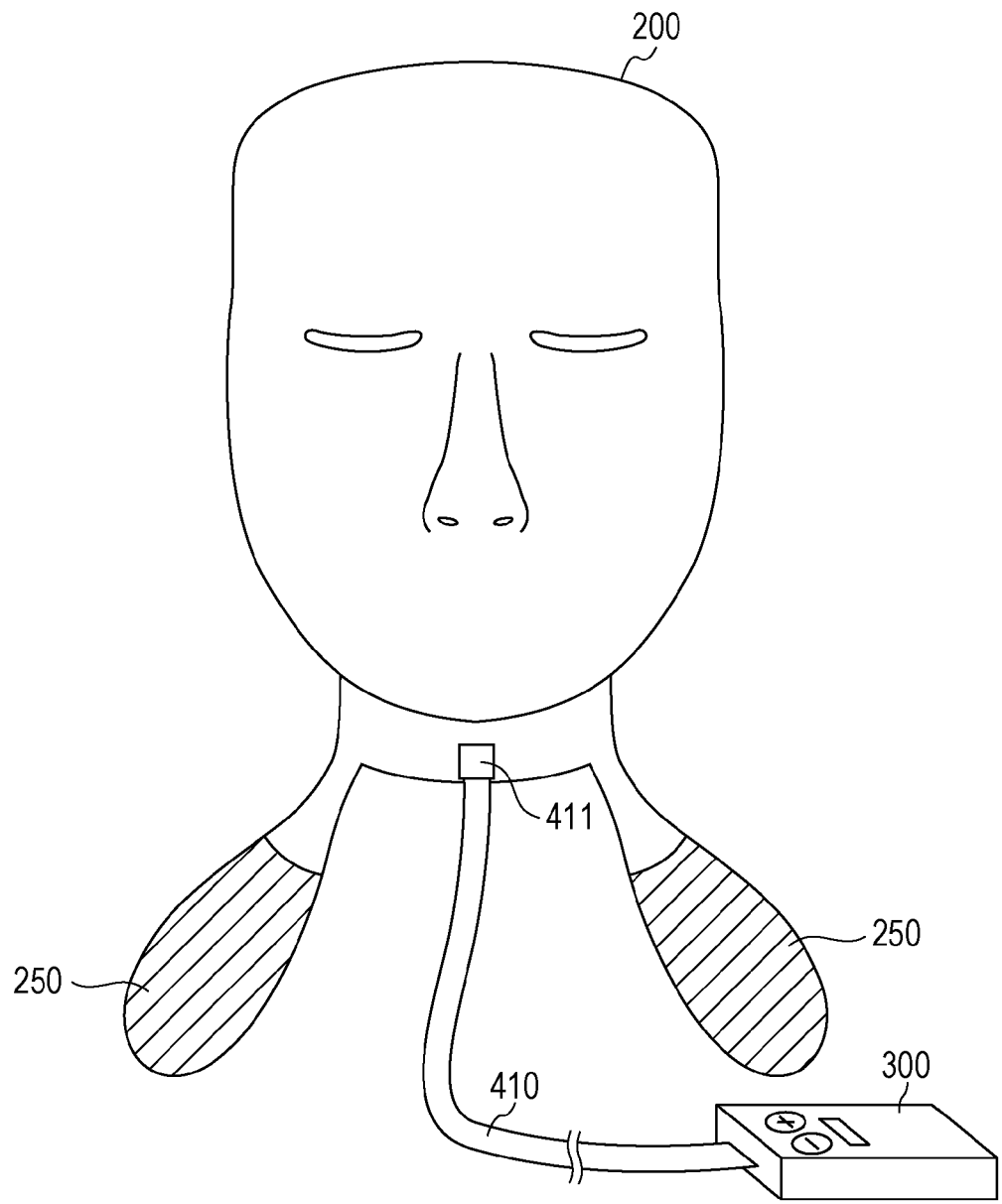
FIG. 12 illustrates a second modification of the appearance of the percutaneous penetration enhancing apparatus according to the second embodiment of the present disclosure.

FIGS. 11 and 12 are examples of appearances of percutaneous penetration enhancing apparatuses 100 in which an electrode unit 250 or electrode units 250 are integrated with a sheet device 200.

In FIG. 11, the electrode unit 250 is formed integrally with the sheet device 200 so that the electrode unit 250 can be placed, for example, on the skin in a region behind an ear in the state in which the sheet device 200 is placed on the face. In FIG. 12, the electrode units 250 are formed integrally with the sheet device 200 so that the electrode units 250 can be placed, for example, on the skin in regions below the collarbones in the state in which the sheet device 200 is placed on the face. In these cases, for example, each electrode unit 250 may include a sheet member that extends continuously from the sheet member of the corresponding sheet device 200. However, in this case, the sheet member preferably provides sufficient insulation.

With the percutaneous penetration enhancing apparatuses 100 having the above-described structures, the overall size can be reduced and the user-friendliness can be improved.

Another Example in which Process is Stopped

When a cosmetic agent penetrates the skin, the skin is activated and various changes occur. Some cosmetic agents have an effect of promoting blood circulation in a short time. For example, cosmetic agents for reducing blemishes, such as alpha hydroxy acids (AHA) and ascorbic acids, have an effect of promoting bloodstream in capillaries.

It is not desirable to excessively activate the skin. Here, the activation of the skin is a concept including, for example, promotion of blood circulation, activation of fibroblasts, promotion of lymph circulation, whitening, reduction in generation of active oxygen, expansion of microvessels, promotion of metabolism, increase in tissue regeneration performance, and muscular relaxation.

The percutaneous penetration enhancing apparatus 100 may determine the time at which the penetration enhancing process is to be stopped depending on the degree of activation of the skin after the start of the penetration enhancing process.

In this case, it is necessary that the sheet device 200 include, for example, a blood flowmeter for each block. Each blood flowmeter detects the bloodstream in the capillaries in the skin in a vicinity of the blood flowmeter under the control of the operation determination unit 320, and outputs the detection result to the operation determination unit 320. The operation determination unit 320 monitors the variation in the bloodstream since the start of the penetration enhancing process for each block, and stops the penetration enhancing process for each block when the bloodstream in the block is increased by 40%.

Thus, penetration of the cosmetic agent into the skin can be enhanced while the skin is prevented from being excessively activated.

The blood flowmeter may be, for example, the one described in "Wearable Laser Blood Flowmeter" written by Takanori Kiyokura, Shinji Mino, and Junichi Shimada, in NTT Technical Review, November 2005, Nippon Telegraph and Telephone Corporation (NTT Microsystem Integration Laboratories), pp. 25-27 (hereinafter referred to as Non-Patent Document 2). The blood flowmeter includes a laser diode and a phototransistor. The phototransistor may be an organic phototransistor formed of a polymer thin-film transistor described in Japanese Unexamined Patent Application Publication No. 2007-300112.

The percutaneous penetration enhancing apparatus 100 may determine the degree of activation of the skin on the basis of the color tone of the skin. In this case, it is necessary that the sheet device 200 include a color tone sensor for each block. In addition, in this case, the sheet device 200 needs to include an optically transparent sheet member or a light-emitting element arranged on the inner surface of the sheet device 200.

Examples of a color tone sensor include a device that measures the intensities of light components having the wavelengths of R, G, and B with optical sensors, and a device described in Non-Patent Document 1, in which three primary colors, R, G, and B, are captured with organic semiconductors. The color tone sensor according to Non-Patent Document 1 can be produced with high precision by printing.

The light-emitting element may be, for example, the laser diode described in Non-Patent Document 2, or an organic LED element or an organic laser diode element formed by printing by using a polymer described in Japanese Unexamined Patent Application Publication No. 2009-48837.

The percutaneous penetration enhancing apparatus 100 may also determine the degree of activation of the skin on the basis of other types of information, such as the temperature of the skin.

Presentation of Regions where Cosmetic Agent is to be Applied

The percutaneous penetration enhancing apparatus 100 may present to the user the locations of the blocks in which the penetration enhancing process is to be performed (that is, locations of the blemishes) as the blocks in which the cosmetic agent is to be applied.

For example, the sheet device 200 includes one or more light-emitting elements arranged on the outer surface thereof for each block. Each light-emitting element is configured to emit light under the control of the operation determination unit 320. When the blocks in which the penetration enhancing process is to be performed are determined, the operation determination unit 320 causes the light-emitting elements corresponding to these blocks to emit light. The user applies the cosmetic agent to the outer surface of the sheet device 200 placed on the face only in regions where light is emitted.

Each light-emitting element may be, for example, the laser diode described in Non-Patent Document 2, or the organic LED element or organic laser diode element described in Japanese Unexamined Patent Application Publication No. 2009-48837.

Thus, the user can apply the cosmetic agent only in the regions in which it is necessary to apply the cosmetic agent. Therefore, with this percutaneous penetration enhancing apparatus 100, the consumption of the cosmetic agent can be reduced and the cosmetic-agent applying process performed by the user can be facilitated.

The cosmetic agent may be applied also in blocks in which the light-emitting elements do not emit light. However, in the blocks in which the light-emitting elements do not emit light, the percutaneous penetration enhancing elements are not activated, and the penetration enhancing process is not performed.

In the case where the sheet member is sufficiently optically transparent, the light-emitting elements may be arranged on the inner surface of the sheet device 200.

In addition, in this case, the light-emitting elements are preferably blue LEDs that emit light in the blue range. This is because light in the blue range has an effect of killing

*Propionibacterium acnes*, and this increases the satisfaction of, in particular, young users. In addition, when the light in the blue range is also used in the detection of blemishes with the color tone sensors, blemishes formed in a deep part of the skin can also be accurately detected.

Control of Supply of Cosmetic Agent

The percutaneous penetration enhancing apparatus 100 may be configured to control the supply of the cosmetic agent so that the cosmetic agent is supplied to the skin only at the locations of the blocks in which the penetration enhancing process is to be performed (that is, the locations where blemishes are present).

Figure 13:
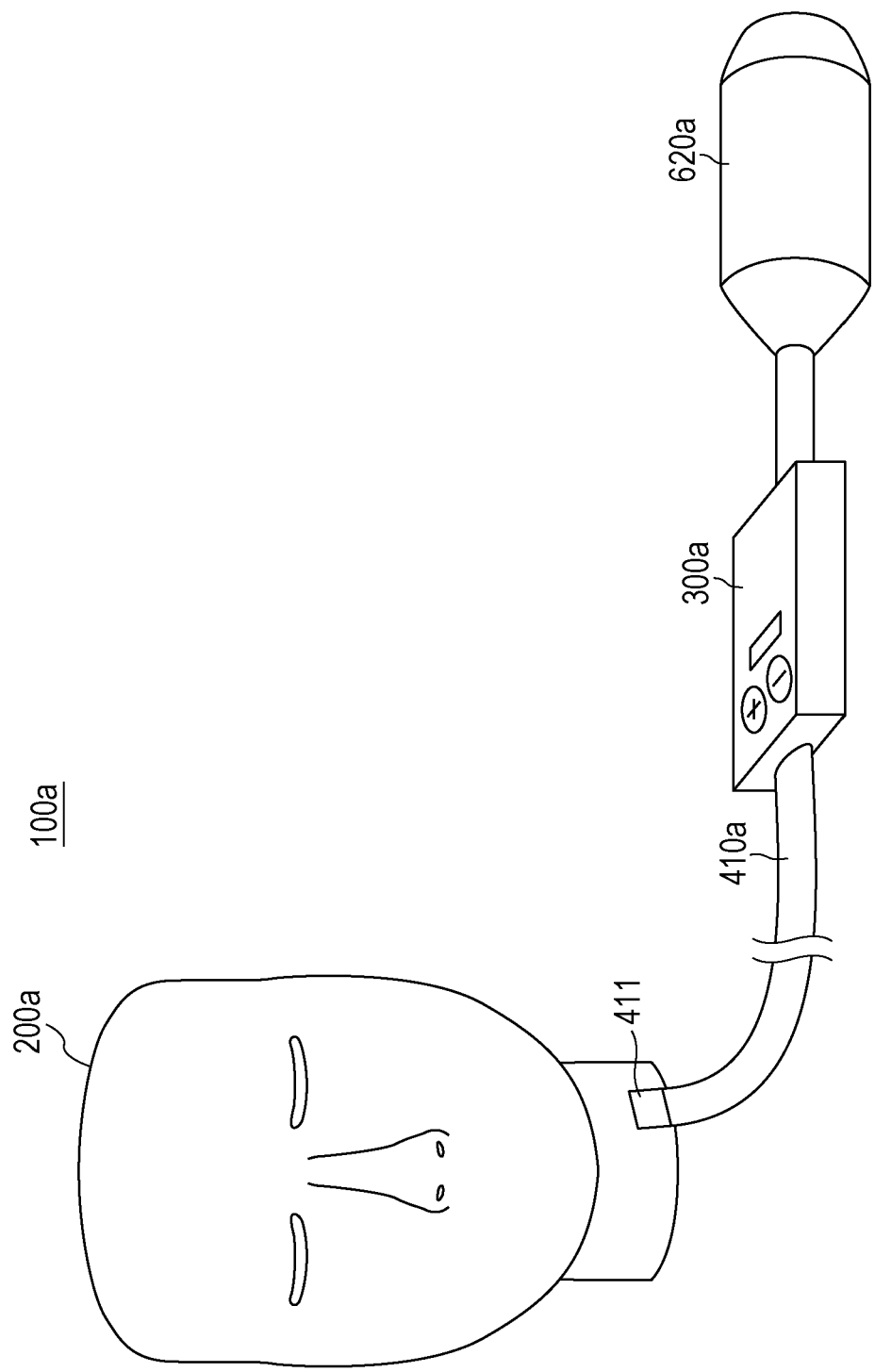
FIG. 13 illustrates a third modification of the appearance of the percutaneous penetration enhancing apparatus according to the second embodiment of the present disclosure.

FIG. 13 illustrates an example of the appearance of the percutaneous penetration enhancing apparatus in the case where the supply of the cosmetic agent is controlled.

As illustrated in FIG. 13, a percutaneous penetration enhancing apparatus 100a includes a cosmetic agent tank 620a that contains a cosmetic agent and a pump (not shown) that pumps out the cosmetic agent contained in the cosmetic agent tank 620a. The pump is a small liquid pump, and is disposed in a control unit 300a. A cable 410a guides the cosmetic agent pumped out by the pump to a sheet device 200a.

Small pipes for delivering the cosmetic agent introduced through the cable 410a to the percutaneous penetration enhancing elements of the respective blocks are arranged in the sheet device 200a.

Figure 14:
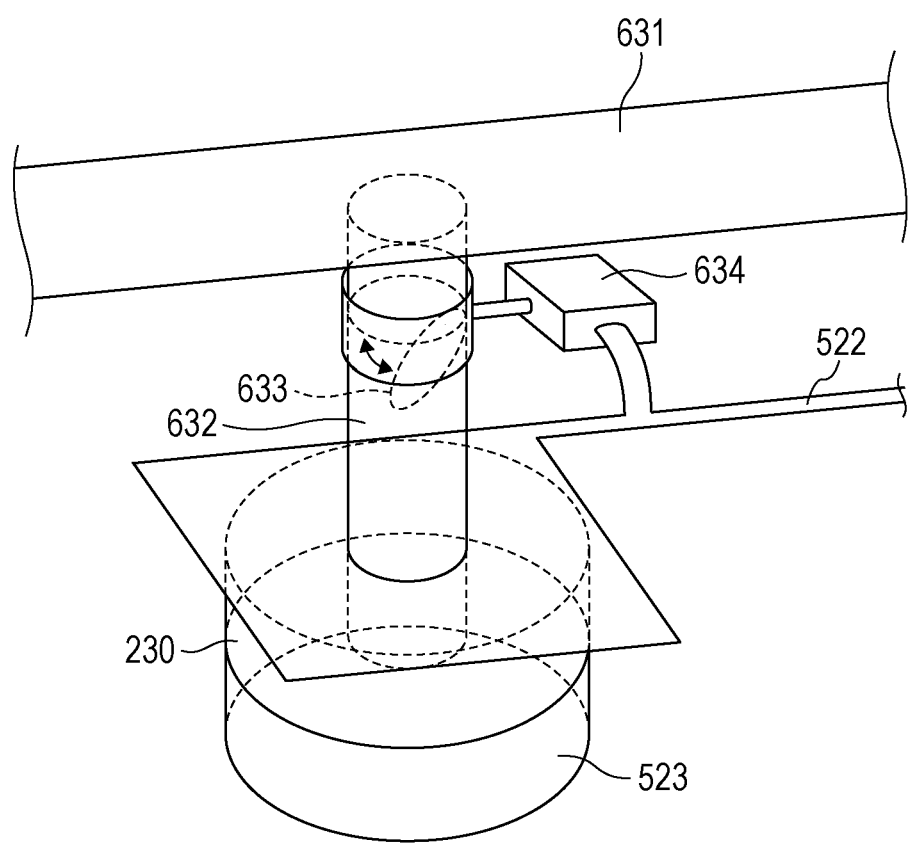
FIG. 14 illustrates a second modification of the structure of the percutaneous penetration enhancing element and the region around the percutaneous penetration enhancing element according to the second embodiment.

FIG. 14 is a diagram corresponding to FIG. 5, illustrating another example of the structure of the percutaneous penetration enhancing element 230 and the region around the percutaneous penetration enhancing element 230.

Referring to FIG. 14, a pipe 631 for transporting a cosmetic agent is disposed in a sheet member (not shown) of the sheet device 200a. A branch pipe 632 is disposed between the pipe 631 and a hole formed at the center of the percutaneous penetration enhancing element 230. The branch pipe 632 guides the cosmetic agent that has been introduced into the pipe 631 to the space 523 between the percutaneous penetration enhancing element 230 and the skin. The branch pipe 632 is provided with a small valve 633 and a valve controller 634 (supply-amount controller) that controls the opened/closed state of the valve 633.

The valve controller 634 is connected to, for example, a wire 522 used to apply a voltage to the percutaneous penetration enhancing element 230. The valve controller 634 includes, for example, a piezoelectric element that serves as a driving unit for driving the valve 633. The valve controller 634 closes the valve 633 when no voltage is applied to the percutaneous penetration enhancing element 230, and opens the valve 633 when a voltage is applied to the percutaneous penetration enhancing element 230. In other words, the valve controller 634 stops the supply of the cosmetic agent when no voltage is applied to the percutaneous penetration enhancing element 230, and does not stop the supply of the cosmetic agent when a voltage is applied to the percutaneous penetration enhancing element 230.

The state in which the valve 633 is closed (state in which the supply of the cosmetic agent is stopped) includes not only the state in which the cosmetic agent is prevented from flowing through the branch pipe 632, but also the state in which it is more difficult for the cosmetic agent to pass through the branch pipe 632 compared to the state in which the valve 633 is opened. The valve 633 itself may be a piezoelectric element that serves the above-described function.

The operation determination unit 320 (see FIG. 7) of the control unit 300 controls the on/off state of the operation of each percutaneous penetration enhancing element 230 by turning on/off the application of voltage to the percutaneous penetration enhancing element 230. Accordingly, the valve controller 634 closes the valve 633, so that the cosmetic agent is not easily supplied, when the corresponding percutaneous penetration enhancing element 230 is not operated. The valve controller 634 opens the valve 633, so that the cosmetic agent is easily supplied, when the corresponding percutaneous penetration enhancing element 230 is operated.

The valve 633 and the valve controller 634 may be provided for each block (segment) instead of each percutaneous penetration enhancing element 230.

With the above-described structure, the percutaneous penetration enhancing apparatus 100 positively supplies the cosmetic agent only at locations of the blocks in which the penetration enhancing process is to be performed. When, for example, there are many small blemishes, such as freckles, it is troublesome for the user to apply the cosmetic agent at each of the locations of the blemishes shown by the light. Therefore, with the above-described percutaneous penetration enhancing apparatus 100, not only can the consumption of the cosmetic agent be reduced, but the cosmetic-agent applying process performed by the user can be greatly facilitated.

Another Example of Process Time Control

The percutaneous penetration enhancing apparatus 100 may control the time or intensity of the penetration enhancing process in accordance with the condition of the skin, such as the darkness of the blemishes.

In this case, for example, the operation determination unit 320 compares the color tones of the skin detected by the color tone sensors arranged in the respective blocks of the sheet device 200, and determines whether or not blemishes are present in each block and the level of the blemishes in each block. The operation determination unit 320 determines the time or intensity of the penetration enhancing process for each block on the basis of the result of the determination, and controls the operation of the percutaneous penetration enhancing element or elements corresponding to each block. More specifically, the operation determination unit 320 sets the process time for the blocks in which dark blemishes are present longer than that for other blocks.

With the above-described control operation, the percutaneous penetration enhancing apparatus 100 is capable of performing the penetration enhancing process more appropriately in accordance with the condition of the skin. As a result, the skin condition can be improved with good balance over the entire face.

Another Example of Penetration Enhancing Process

In the above-described embodiment, iontophoresis is performed as the penetration enhancing process. However, in the present disclosure, other types of penetration enhancing processes, such as electroporation, may also be employed.

In electroporation, the voltage applied is several hundred volts, which is much higher than the voltage applied in iontophoresis. The voltage, for example, is applied for a microsecond-order time period (pulse) once every minute, 60 times in total. In electroporation, cells are temporarily perforated. Therefore, penetration of uncharged polymer agents, with which iontophoresis cannot be effectively performed, into the skin can be enhanced.

Another Example of Object to be Processed

In the above-described embodiments, the percutaneous penetration enhancing apparatuses are used mainly to reduce blemishes. However, the present disclosure may also be applied to percutaneous penetration enhancing apparatuses for treating other types of skin conditions, such as fine wrinkles due to dry skin.

In the case where the purpose is to reduce fine wrinkles due to dry skin, skin moisture sensors are arranged on the inner surface of the sheet device 200 as skin condition sensors, and a humidity sensor is arranged on the outer surface of the sheet device 200.

The humidity sensor may be, for example, the one described in Japanese Unexamined Patent Application Publication No. 58-97650, which is formed of an organic semiconductor including a polyimide film.

Each skin moisture sensor may be, for example, an apparatus that includes a combination of a laser diode and a photodetector and that measures (detects) the skin moisture content as the information related the condition of the skin by Raman spectroscopy.

Figure 15:
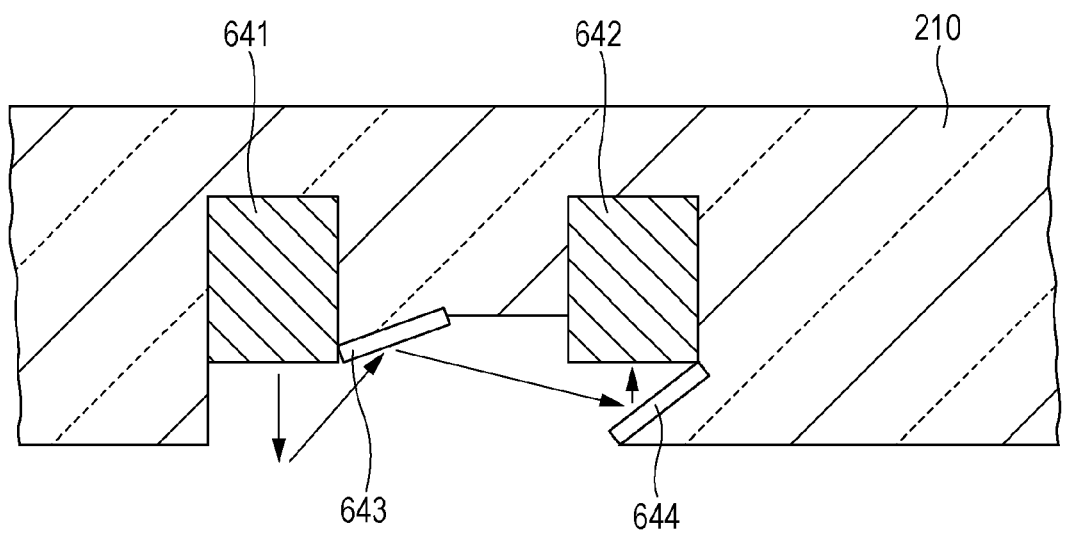
FIG. 15 illustrates an example of the structure of a skin condition sensor according to the second embodiment.

FIG. 15 illustrates an example of the structure of a skin moisture sensor (skin condition sensor).

Referring to FIG. 15, a skin moisture sensor 640 includes, for example, a laser diode 641, a photodetector 642, a reflector plate 643, and a wavelength selecting element 644.

The laser diode 641 and the photodetector 642 are embedded in a sheet member 210 at locations recessed from the inner surface (lower surface in FIG. 15). The reflector plate 643 is arranged at a certain position and angle so that light emitted from the laser diode 641 and reflected and scattered by the skin is reflected by the reflector plate 643 so as to be incident on the wavelength selecting element 644. The wavelength selecting element 644 is arranged at a certain position and angle so that the reflected light from the reflector plate 643 is reflected so as to be incident on the photodetector 642.

The laser diode 641 emits light with a wavelength of about 800 nm, which is in the near-infrared range and at which light passes through the epidermal layer, toward the skin in a vicinity of the laser diode 641. This wavelength is used to detect the moisture between the epidermal layer and the dermal layer.

The wavelength selecting element 644 receives the scattered light from the reflector plate 643, selects a light component having a wavelength (or Raman shift) corresponding to the scattered wave generated by moisture from the scattered light, and causes the selected light component to be incident on the photodetector 642. The wavelength selecting element 644 may be, for example, the one described Japanese Unexamined Patent Application Publication (Translation of PCT Application) No. 2005-516216, which includes a combination of a resonant grating and a reflecting mirror.

The photodetector 642 receives light with an intensity that corresponds to the skin moisture content in a vicinity of the skin moisture sensor 640. The photodetector 642 may be, for example, an organic photodetector described in Japanese Unexamined Patent Application Publication (Translation of PCT Application) No. 2013-506282.

The skin moisture sensor 640 having the above-described structure measures the skin moisture content by Raman spectroscopy. The output value of the photodetector 642 corresponds to the skin moisture content in the vicinity of the skin moisture sensor 640. The operation determination unit 320 determines the skin moisture content on the basis of the detection value input from the skin moisture sensor 640.

The operation determination unit 320 determines the standard skin moisture content (standard value) corresponding to the external humidity, which is detected by the humidity sensor, by referring to a table or performing calculation on the basis of the detected external humidity. The relationship between the external humidity and the standard value of the skin moisture content may be, for example, the one described Japanese Unexamined Patent Application Publication No. 11-19060.

The operation determination unit 320 compares the detection result of the skin moisture sensor in each block with a threshold determined on the basis of the standard value of the skin moisture content, and selects blocks in which the skin moisture content is lower than or equal to the threshold as blocks in which moisturizing agent is to be supplied to the skin. The threshold is set to, for example, a value obtained by reducing the standard value of skin moisture content by 10%. The operation determination unit 320 operates the percutaneous penetration enhancing elements in the selected blocks. In this case, the user needs to prepare a cosmetic agent containing a moisturizing component, such as niacinamide.

In the case where a single block has a plurality of skin moisture sensors, the operation determination unit 320 may determine whether or not the supply of moisturizing component to the skin is required in that block on the basis of the average of the detection values obtained by the skin moisture sensors in that block.

The size and arrangement of the blocks, which are the units of control, of the sheet device 200 are preferably suitable for the purpose of the penetration enhancing process.

For example, in regions around the eyes and mouth, the degree of dryness of the skin greatly varies depending on the position even in small regions. Therefore, when, for example, the purpose is to reduce fine wrinkles due to dry skin, blocks in the regions around the eyes and month are preferably smaller than the blocks in other regions. In this case, the penetration enhancing process can be more appropriately performed in the regions around the eyes and mouth.

The densities of the skin condition sensors and percutaneous penetration enhancing elements on the sheet device 200 and the distributions of the densities are also preferably suitable for the purpose of the penetration enhancing process.

For example, the skin easily becomes dry in the regions around the eyes and mouth. Therefore, when, for example, the purpose is to reduce fine wrinkles due to dry skin, the densities of the skin condition sensors and percutaneous penetration enhancing elements in the blocks around the eyes and mouth are preferably greater than the densities of the skin condition sensors and percutaneous penetration enhancing elements in other blocks. In this case, the penetration enhancing process can be positively performed in the regions around the eyes and mouth.

In the case where the purpose is to reduce fine wrinkles due to dry skin, the percutaneous penetration enhancing apparatus 100 may determine the degree of activation of the skin and control the penetration enhancing process in accordance with the degree of activation of the skin. For example, the percutaneous penetration enhancing apparatus 100 operates the percutaneous penetration enhancing elements in the blocks for which it has been determined that the degree of activation of the skin is not sufficient. Cell activation components, such as ascorbic acid (vitamin C) and retinol palmitate (vitamin A), are suitable for the treatment of wrinkles due to dry skin caused by insufficient degree of activation of the skin.

In the case where the penetration enhancing process is electroporation, a hyaluronic acid with a high molecular weight may be used as a moisturizing component.

The percutaneous penetration enhancing apparatus 100 may also be used for the purpose of treating large deep wrinkles in the dermal layer, such as wrinkles on the forehead, glabella, and outer corners of the eyes, nasolabial folds, and marionette lines (wrinkles that stretch from the corners of the mouth to the jaw).

In this case, the sheet device 200 is configured such that measurement sensors arranged on the inner surface thereof measure the sizes of wrinkles on the face based on, for example, the curve of the sheet, contact pressure, or muscular tension.

For example, when the sheet device 200 is in close contact with the skin, deformation (undulation) of the sheet device 200 is large in regions around large deep wrinkles. Therefore, the pressure applied between the sheet device 200 and the skin (hereinafter referred to as "skin pressure") in the regions around large deep wrinkles greatly differs from the skin pressure in other regions. Therefore, in the percutaneous penetration enhancing apparatus 100, pressure sensors may be used as the skin condition sensors and regions in which large and deep wrinkles are present can be detected as the information related to the condition of the skin on the basis of the distribution of the skin pressure. Each pressure sensor may be, for example, the one described in Japanese Patent No. 5197960 and Japanese Unexamined Patent Application Publication No. 2007-178256.

More specifically, first, the operation determination unit 320 calculates the average value and dispersion of detection values obtained by pressure sensors disposed in blocks corresponding to regions in which the number of large wrinkles is small (nose, cheek, etc.). Then, the operation determination unit 320 determines a value obtained by adding or subtracting a value corresponding to the dispersion to/from the calculated average value as a threshold, and determines blocks in which the output values of the pressure sensors are above the threshold as blocks in which the penetration enhancing process is to be performed.

Other Modifications

At least one of the functions of the control unit 300 according to the above-described second embodiment may be provided by a device having another function, such as a mobile phone.

Alternatively, the above-described functions may be provided in a network server. In other words, at least one of the functions of the percutaneous penetration enhancing apparatus 100 may be realized through cloud computing. In this case, the operation determination unit 300 needs to include at least a communication unit.

In addition, the percutaneous penetration enhancing apparatus 100 may be applied not only to a sheet for the face, but also to a sheet having, for example, an elliptical or rectangular shape that covers another part of the body. For example, mottle patterned blemishes that appear on the back due to sunburn or the like can be effectively treated by using the percutaneous penetration enhancing apparatus 100.

The percutaneous penetration enhancing apparatus 100 may include operation determination units 320 for the respective blocks, each operation determination unit 320 operating the corresponding block.

A percutaneous penetration enhancing apparatus according to the present disclosure includes a sheet member capable of being placed on a skin; a plurality of skin condition sensors arranged on the sheet member, each of the plurality of skin condition sensors detecting information related to a condition of the skin; and a plurality of percutaneous penetration enhancing elements arranged on the sheet member, each of the plurality of percutaneous penetration enhancing elements being operated on the basis of the information detected by one or more of the plurality of skin condition sensors.

In the percutaneous penetration enhancing apparatus, each of the plurality of percutaneous penetration enhancing elements may perform a penetration enhancing process including at least one of iontophoresis and electroporation.

The percutaneous penetration enhancing apparatus may further include an operation determination unit, and the sheet member may be divided into segments, each of which includes one or more of the plurality of percutaneous penetration enhancing elements and one or more of the plurality of skin condition sensors. The operation determination unit may determine, for each of the segments, whether or not to cause the one or more of the plurality of percutaneous penetration enhancing elements included in a segment to perform the penetration enhancing process on the basis of the information detected by the one or more of the plurality of skin condition sensors included in the segment. The sheet member may be detachably connected to the operation determination unit with a connector and a cable.

Each of the plurality of skin condition sensors may detect a color tone of the skin as the information, and the operation determination unit may select one or more of the segments in which the color tone is darker than in other segments on the basis of the information detected by the plurality of skin condition sensors, and determine that the penetration enhancing process is to be performed in the selected one or more of the segments.

Each of the plurality of skin condition sensors may detect a moisture content of the skin as the information, and the operation determination unit may select one or more of the segments in which the moisture content is smaller than in other segments on the basis of the information detected by the plurality of skin condition sensors, and determine that the penetration enhancing process is to be performed in the selected one or more of the segments.

The sheet member may include a plurality of light-emitting elements arranged in the respective segments. The sheet member may have holes that guide a cosmetic agent applied to an outer surface of the sheet member to an inner surface of the sheet member. The operation determination unit may cause one or more of the plurality of light-emitting elements to emit light, the one or more of the plurality of light-emitting elements being arranged in one or more of the segments in which the penetration enhancing process is to be performed.

The percutaneous penetration enhancing apparatus may further include a tank that contains a cosmetic agent and a pump that supplies the cosmetic agent contained in the tank to the sheet member. The sheet member may include a pipe that supplies the cosmetic agent supplied by the pump to each of the plurality of percutaneous penetration enhancing elements, and a plurality of supply-amount controllers arranged in the respective segments, the supply-amount controller controlling the supply of the cosmetic agent by the pipe. The operation determination unit may instruct one or more of the plurality of supply-amount controllers that are arranged in one or more of the segments in which the penetration enhancing process is not to be performed to stop the supply of the cosmetic agent.

The percutaneous penetration enhancing apparatus may further include a plurality of temperature sensors arranged on the sheet member in the respective segments, each of the plurality of temperature sensors detecting a temperature of the skin. When a value detected by one or more of the plurality of temperature sensors is greater than or equal to a predetermined threshold, the operation determination unit may stop the penetration enhancing process at least in one or more of the segments in which the one or more of the plurality of temperature sensors are arranged.

A percutaneous penetration enhancing method according to the present disclosure includes detecting, with a plurality of skin condition sensors arranged on a sheet member capable of being placed on a skin, information related to a condition of the skin; and operating each of a plurality of percutaneous penetration enhancing elements arranged on the sheet member on the basis of the information detected by one or more of the plurality of skin condition sensors.

The percutaneous penetration enhancing apparatus according to the present disclosure is a useful apparatus that is capable of effectively performing the penetration enhancing process.

CROSS REFERENCE TO RELATED APPLICATION

The present application claims the benefit of Japanese Patent Application No. 2013-272318 filed on Dec. 27, 2013. The entire disclosure of the above-identified application, including the specification, drawings and claims, is incorporated herein by reference in its entirety.

What is claimed is:

1. A percutaneous penetration enhancing apparatus comprising:
a sheet member capable of being placed on a skin;
a plurality of skin condition sensors arranged on the sheet member, each of the plurality of skin condition sensors detecting information related to a condition of the skin;
a plurality of percutaneous penetration enhancing elements arranged on the sheet member, each of the plurality of percutaneous penetration enhancing elements being operated on the basis of the information detected by one or more of the plurality of skin condition sensors;
an operation determination unit;
wherein the sheet member is divided into segments, each of which includes one or more of the plurality of percutaneous penetration enhancing elements and one or more of the plurality of skin condition sensors;
wherein the operation determination unit determines, for each of the segments, whether or not to cause the one or more of the plurality of percutaneous penetration enhancing elements included in a segment to perform the penetration enhancing process on the basis of the information detected by the one or more of the plurality of skin condition sensors included in the segment;
a tank that contains a cosmetic agent; and
a pump that supplies the cosmetic agent contained in the tank to the sheet member, wherein the sheet member includes a pipe that supplies the cosmetic agent supplied by the pump to each of the plurality of percutaneous penetration enhancing elements, and a plurality of supply-amount controllers arranged in the respective segments, the supply-amount controllers controlling the supply of the cosmetic agent by the pipe, and
wherein the operation determination unit instructs one or more of the plurality of supply-amount controllers that are arranged in one or more of the segments in which the penetration enhancing process is not to be performed to stop the supply of the cosmetic agent.

2. The percutaneous penetration enhancing apparatus according to claim 1, wherein each of the plurality of percutaneous penetration enhancing elements performs a penetration enhancing process including at least one of iontophoresis and electroporation.

3. The percutaneous penetration enhancing apparatus according to claim 1, wherein the sheet member is detachably connected to the operation determination unit with a connector and a cable.

4. The percutaneous penetration enhancing apparatus according to claim 1, wherein each of the plurality of skin condition sensors detects a color tone of the skin as the information, and
wherein the operation determination unit selects one or more of the segments in which the color tone is darker than in other segments on the basis of the information detected by the plurality of skin condition sensors, and determines that the penetration enhancing process is to be performed in the selected one or more of the segments.

5. The percutaneous penetration enhancing apparatus according to claim 1, wherein each of the plurality of skin condition sensors detects a moisture content of the skin as the information, and
wherein the operation determination unit selects one or more of the segments in which the moisture content is smaller than in other segments on the basis of the information detected by the plurality of skin condition sensors, and determines that the penetration enhancing process is to be performed in the selected one or more of the segments.

6. The percutaneous penetration enhancing apparatus according to claim 1, wherein the sheet member includes a plurality of light-emitting elements arranged in the respective segments,
wherein the sheet member has holes that guide a cosmetic agent applied to an outer surface of the sheet member to an inner surface of the sheet member, and
wherein the operation determination unit causes one or more of the plurality of light-emitting elements to emit light, the one or more of the plurality of light-emitting elements being arranged in one or more of the segments in which the penetration enhancing process is to be performed.

7. The percutaneous penetration enhancing apparatus according to claim 1, further comprising:
a plurality of temperature sensors arranged on the sheet member in the respective segments, each of the plurality of temperature sensors detecting a temperature of the skin,
wherein, when a value detected by one or more of the plurality of temperature sensors is greater than or equal to a predetermined threshold, the operation determination unit stops the penetration enhancing process at least in one or more of the segments in which the one or more of the plurality of temperature sensors are arranged.

8. A percutaneous penetration enhancing method, comprising:
detecting, with a plurality of skin condition sensors arranged on a sheet member capable of being placed on a skin, information related to a condition of the skin; and
operating each of a plurality of percutaneous penetration enhancing elements arranged on the sheet member on the basis of the information detected by one or more of the plurality of skin condition sensors, wherein the sheet member is divided into segments, each of which includes one or more of the plurality of percutaneous penetration enhancing elements and one or more of the plurality of skin condition sensors;

determining, with an operation determination unit, for each of the segments, whether or not to cause the one or more of the plurality of percutaneous penetration enhancing elements included in a segment to perform the penetration enhancing process on the basis of the information detected by the one or more of the plurality of skin condition sensors included in the segment; and supplying, with a pump a cosmetic agent contained in a tank to the sheet member, wherein the sheet member includes a pipe that supplies the cosmetic agent supplied by the pump to each of the plurality of percutaneous penetration enhancing elements, and a plurality of supply-amount controllers arranged in the respective segments, the supply-amount controllers controlling the supply of the cosmetic agent by the pipe, and wherein the operation determination unit instructs one or more of the plurality of supply-amount controllers that are arranged in one or more of the segments in which the penetration enhancing process is not to be performed to stop the supply of the cosmetic agent.

* * * * *